United States Patent
Bahr

(10) Patent No.: US 10,702,571 B2
(45) Date of Patent: Jul. 7, 2020

(54) MATERIALS FOR CATHEPSIN B ENHANCEMENT AND METHODS OF USE

(71) Applicant: The University of North Carolina at Pembroke, Pembroke, NC (US)

(72) Inventor: Ben A. Bahr, Lake Waccamaw, NC (US)

(73) Assignee: The University of North Carolina at Pembroke, Pembroke, NC (US)

( * ) Notice: Subject to any disclaimer, the term of this patent is extended or adjusted under 35 U.S.C. 154(b) by 0 days.

(21) Appl. No.: 15/780,971

(22) PCT Filed: Dec. 1, 2016

(86) PCT No.: PCT/US2016/064433
§ 371 (c)(1),
(2) Date: Jun. 1, 2018

(87) PCT Pub. No.: WO2017/096049
PCT Pub. Date: Jun. 8, 2017

(65) Prior Publication Data
US 2018/0264071 A1 Sep. 20, 2018

Related U.S. Application Data

(60) Provisional application No. 62/262,848, filed on Dec. 3, 2015.

(51) Int. Cl.
| A61K 31/70 | (2006.01) |
| A61K 31/27 | (2006.01) |
| A61K 38/05 | (2006.01) |
| A61K 31/352 | (2006.01) |
| C07K 5/065 | (2006.01) |
| A61K 45/06 | (2006.01) |
| A61P 25/28 | (2006.01) |
| A61K 9/00 | (2006.01) |

(52) U.S. Cl.
CPC ............ *A61K 38/05* (2013.01); *A61K 9/0053* (2013.01); *A61K 31/352* (2013.01); *A61K 45/06* (2013.01); *A61P 25/28* (2018.01); *C07K 5/06078* (2013.01)

(58) Field of Classification Search
None
See application file for complete search history.

(56) References Cited

U.S. PATENT DOCUMENTS

| 6,491,948 | B1 | 12/2002 | Buchholz et al. |
| 7,026,360 | B1 | 4/2006 | Festo |
| 7,034,054 | B2 | 4/2006 | Miller et al. |
| 7,667,044 | B2 * | 2/2010 | Niestroj ............... C07D 417/06 548/200 |
| 7,897,637 | B2 | 3/2011 | Maher |
| 8,163,953 | B2 * | 4/2012 | Bahr .................... C07C 271/20 560/72 |
| 8,357,422 | B2 | 1/2013 | Howard |
| 8,574,642 | B2 | 11/2013 | Palu |
| 8,673,983 | B2 | 3/2014 | Holmes et al. |
| 8,778,986 | B1 | 7/2014 | Tan |
| 8,802,638 | B1 | 8/2014 | Tan |
| 8,916,528 | B2 | 12/2014 | Sardi |
| 10,202,355 | B2 | 2/2019 | John et al. |
| 2002/0094958 | A1 | 7/2002 | Bahr |
| 2003/0224345 | A1 | 12/2003 | West et al. |
| 2004/0087561 | A1 | 5/2004 | Gonzalez et al. |
| 2004/0106685 | A1 | 6/2004 | Ram et al. |
| 2007/0053849 | A1 | 3/2007 | Doyle et al. |
| 2009/0082400 | A1 | 3/2009 | Lee |
| 2009/0088394 | A1 | 4/2009 | Robbins |
| 2009/0156668 | A1 | 6/2009 | Vitolo et al. |
| 2009/0163448 | A1 | 6/2009 | Powell |
| 2009/0264355 | A1 | 10/2009 | Holtzman |
| 2010/0074959 | A1 | 3/2010 | Hansom et al. |
| 2010/0316564 | A1 | 12/2010 | Sigurdsson |
| 2011/0065662 | A1 | 3/2011 | Rinsch et al. |
| 2011/0256120 | A1 | 10/2011 | Gan et al. |
| 2011/0263526 | A1 | 10/2011 | Satyam |
| 2012/0052053 | A1 | 3/2012 | Manning-Bog et al. |
| 2012/0184624 | A1 | 7/2012 | Schweiger et al. |
| 2013/0196976 | A1 | 8/2013 | Lee et al. |
| 2014/0242153 | A1 | 8/2014 | Mannino |
| 2014/0294724 | A1 | 10/2014 | Chain |
| 2014/0356340 | A1 | 12/2014 | Burbidge et al. |

(Continued)

FOREIGN PATENT DOCUMENTS

| AU | 3886200 A | 10/2000 |
| AU | 2002312897 A8 | 11/2002 |

(Continued)

OTHER PUBLICATIONS

Grosso et al., Current Med. Chem., 2013, 20:4694-719.*
Bahr, "Lysosomal Modulatory Drugs for a Broad Strategy Against Protein Accumulation Disorders," Current Alzheimer Research, 6, 438-445 (2009).
Bahr, "A Single Pathway Targets Several Health Challenges of the Elderly," Rejuvenation Research, 17(4), 382-384 (2014).
Bateman et al., "Clinical and Biomarker Changes in Dominantly Inherited Alzheimer's Disease," New England Journal of Medicine, 367, 795-804, (2012). DOI: 10.1056/NEJMoa1202753.
Bendiske and Bahr, "Lysosomal Activation is a Compensatory Response Against Protein Accumulation and Synaptopathogenesis— An Approach for Slowing Alzheimer's Disease?", J. Neuropathol. Exp. Neurol., 62, 451-463 (2003).

(Continued)

*Primary Examiner* — Olga N Chernyshev
(74) *Attorney, Agent, or Firm* — Jenkins, Wilson, Taylor & Hunt, P.A.

(57) ABSTRACT

The present invention provides methods for treating a subject afflicted with a protein accumulation disease or TBI, comprising administering to the subject at least one compound that increases the level of active cathepsin B in cells of the subject, or a pharmaceutically acceptable salt or ester thereof, in an amount that is effective to treat the subject. The present invention also provides compositions for treating a subject afflicted with a protein accumulation disease or TBI.

12 Claims, 5 Drawing Sheets

(56) References Cited

U.S. PATENT DOCUMENTS

| | | | |
|---|---|---|---|
| 2014/0356455 | A1 | 12/2014 | Reijo Pera et al. |
| 2015/0038530 | A1 | 2/2015 | Abraham et al. |
| 2015/0226757 | A1 | 8/2015 | Ory |
| 2015/0306122 | A1 | 10/2015 | John et al. |

FOREIGN PATENT DOCUMENTS

| | | | |
|---|---|---|---|
| AU | 2013205053 B2 | | 5/2013 |
| AU | 2014100873 A4 | | 9/2014 |
| CA | 2392709 A1 | | 7/2001 |
| CA | 2504334 | | 5/2004 |
| CA | 2536096 A1 | | 8/2005 |
| CA | 2686468 C | | 1/2014 |
| CA | 2767583 | | 6/2015 |
| CN | 103739642 | | 4/2014 |
| CN | 104383052 A | | 3/2015 |
| CN | 104447717 | | 3/2015 |
| CN | 104623670 A | | 5/2015 |
| CN | 104693121 | | 6/2015 |
| CN | 104725628 | | 6/2015 |
| EP | 0586690 | | 3/1994 |
| EP | 1774972 | | 4/2007 |
| EP | 1708694 B1 | | 7/2012 |
| EP | 1558922 | | 2/2013 |
| JP | 2005104850 A | | 4/2005 |
| JP | 2007145839 A | | 6/2007 |
| JP | 2009034080 | | 2/2009 |
| JP | 2014237635 A | | 12/2014 |
| JP | 2015521608 A | | 7/2015 |
| WO | WO 1999/041984 A1 | | 8/1999 |
| WO | WO 2002/005813 | | 1/2002 |
| WO | WO 2004/046070 | | 6/2004 |
| WO | WO 2005/027901 | | 3/2005 |
| WO | WO 2006/081329 A2 | | 8/2006 |
| WO | WO 2006/121558 A2 | | 11/2006 |
| WO | WO 2008/033351 | | 3/2008 |
| WO | WO 2008/116165 | | 9/2008 |
| WO | WO2008/1277291 | | 10/2008 |
| WO | WO 2009/039195 | | 3/2009 |
| WO | WO 2009/064485 | | 5/2009 |
| WO | WO 2009/083612 | | 7/2009 |
| WO | WO 2009/087568 | | 7/2009 |
| WO | WO 2010/124623 | | 11/2010 |
| WO | WO 2011/041557 A1 | | 4/2011 |
| WO | WO 2012/067305 A1 | | 5/2012 |
| WO | WO 2013/020368 | | 2/2013 |
| WO | WO 2014/204956 | | 12/2014 |
| WO | WO 2015/006643 | | 1/2015 |
| WO | WO 2015/097088 | | 7/2015 |

OTHER PUBLICATIONS

Fleisher et al., PET Analysis of amyloid-β deposition in the presenilin 1 E280A autosomal dominant Alzheimer's disease kindred: a cross-sectional study. Lancet Neurol. 2012 11:1057-65.

Goldstein et al., "Chronic Traumatic Encephalopathy in Blast-Exposed Military Veterans and a Blast Neurotrauma Mouse Model," Sci. Transl. Med., 4(134), 134ra60 (2012). DOI: 10.1126/scitranslmed.3003716. (32 pages).

Gondi et al., "Cathepsin B as a Cancer Target," Expert Opin. Ther. Targets, 17(3), 281-291 (2013).

Isas et al., "Soluble and Mature Amyloid Fibrils in Drusen Deposits," Invest. Ophthalmol. Vis. Sci., 51(3), 1304-1310 (2010).

Mueller-Steiner et al., "Antiamyloidogenic and Neuroprotective Functions of Cathepsin B: Implications for Alzheimer's Disease," Neuron, 51, 703-714 (2006).

Notification Concerning Transmittal of International Preliminary Report on Patentability (Chapter 1 of the Patent Cooperation Treaty) corresponding to PCT/US2016/064433 dated Jun. 14, 2018.

Notification of Transmittal of the International Search Report and Written Opinion of the International Searching Authority, or the Declaration corresponding to PCT/US2016/064433 dated Feb. 21, 2017.

Notice of Publication corresponding to International Patent Application No. PCT/US2016/064433 dated Jun. 8, 2017.

Park et al., "Cilostazol Modulates Autophagic Degradation of (-Amyloid Peptide via SIRT1-Coupled LKB1/AMPK( Signaling in Neuronal Cells," Plos One, 11(8), e0160620 (Aug. 5, 2016). DOI: 10.1371/journal.pone.0160620 (15 pages).

Pepeu, "Mild Cognitive Impairment: Animal Models," Dialogues Clin. Neurosci., 6, 369-377 (2004).

Perez et al., "Hippocampal Endosomal, Lysosomal, and Autophagic Dysregulation in Mild Cognitive Impairment: Correltion with A( and Tau Pathology,"0 J. Neuropathol. Exp. Neurol., 74(4), 345-358 (Apr. 2015).

Peterson et al., "Mild Cognitive Impairment: Ten Years Later," Arch. Neurol., 66(12), 1447-1455 (2009).

Punithavathi et al. "Pretreatment with a Combination of Quercetin and Alpha-Tocopherol Ameliorates Adenosine Triphosphatases and Lysosomal Enzymes in Myocardial infarcted Rats," Life Sciences, vol. 86, 1780184 (2010).

Viswanathan et al., "Nonpeptidic Lysosomal Modulators Derived from Z-Phe-Ala-diazomethylketone for Treating Protein Accumulation Diseases," ACS Med. Chem. Lett., 3, 920-924 (2012).

Gavilan et al., "Age-related Dysfunctions of the Autophagy Lysosomal Pathway in Hippocampal Pyramidal Neurons Under Proteasome Stress," Neurobiol. Aging, 36(5), 1953-1963 (2015). DOI: 10.1016/j.neurobiolaging.2015.02.025 (epub Feb. 28, 2015).

Gianfranceschi et al., "Critical Role of Lysosomes in the Dysfunction of Human Cardiac Stem Cells Obtained from Failing Hearts," Int. J. Cardiol., 216, 140-150 (epub Apr. 26, 2016). DOI: 10.1016/j.ijcard.2016.04.155.

Ge et al., "Enhanced Myocardial Cathepsin B Expression in Subjects with Dilated Cardiomyopathy," Eur. J. Heart Fail., 8(3), 284-289 (2006).

Mariani et al., "Mild Cognitive Impairment: A Systemic Review," J. Alzheimers Dis., 12(1), 23-35, (2007).

Huang, J., "Dementia," Memory Impairment and Neurodegenerative Dementia (MIND) Center, University of Mississippi Medical Center, 9 pages [online], [retrieved on Aug. 29, 2009]. Retrieved from the Internet< URL:www.merckmanuals.com/professional/neurologic_disorders/delirium_and_dementia/dementia.html>.

Mehta, S., "Age-Related Macular Degeneration (AMD or ARMD)" Vitreoretinal Diseases and Surgery Service, Wills Eye Hospital, Sidney Kimmel Medical College at Thomas Jefferson University, 4 pages [online], [retrieved on Aug. 29, 2009]. Retrieved from the Internet< URL:www.merckmanuals.com/home/eye_disorders/retinal_disorders/age-related_macular_degeneration.html>.

Moon et al., "Running-Induced Systemic Cathepsin B Secretion is Associated with Memory Function," AJHG, 24(2), 332-340 (Aug. 9, 2016).

Mufson et al., "Entorhinal cortex beta-amyloid load in individuals with mild cognitive impairment." Exp Neurol; 158:469-490 (1999).

\* cited by examiner

10 μM Z-Phe-Pro-OH caused 1.55-fold increase in CatB-30,

30 μM caused 3.66 ± 0.22 fold increase in CatB-30 (p=0.0269)

MATERIALS FOR CATHEPSIN B ENHANCEMENT AND METHODS OF USE

This application claims benefit, under 35 U.S.C. § 371, of PCT International Patent Application Serial No. PCT/US2016/064433, filed Dec. 1, 2016, incorporated herein by reference in its entirety, which claims priority of U.S. provisional application Ser. No. 62/262,848, filed Dec. 3, 2015, the entire content of which is hereby incorporated by reference herein.

This invention was made with government support under Grant No. W911NF-15-1-0053 from the U.S. Army Research Office. The government has certain rights to this invention.

Throughout this application, various publications are referenced, including referenced in parenthesis. Full citations for publications referenced in parenthesis may be found listed at the end of the specification immediately preceding the claims. The disclosures of all referenced publications in their entireties are hereby incorporated by reference into this application in order to more fully describe the state of the art to which this invention pertains.

BACKGROUND OF INVENTION

Lysosomes are the cellular components involved in removing misfolded/aggregating proteins, but with aging, lysosomes become less effective at clearing toxic accumulations that are linked to the deterioration of neuronal connections. For example, a recent study using a model of proteasome stress in rat hippocampus showed that the level of cathepsin B, a lysosomal cysteine protease, increased in response to proteolytic stress in young rats but not in aged rats (Gavilán et al. (2015) "Age-related dysfunction of the autophagy lysosomal pathway in hippocampal pyramidal neurons under proteasome stress" Neurobiol Aging. 36:1953-1963). In vivo, it has also been shown that cathepsin B activity significantly increased in young and middle-aged, but not elderly mice that express human amyloid beta (Aβ) precursor protein (hAPP) as compared to age-matched nontransgenic control mice (Mueller-Steiner S, Zhou Y, Roberson E D, Sun B, Chen J, et al. (2006) Antiamyloidogenic and neuroprotective functions of cathepsin B: Implications for Alzheimer's disease. Neuron 51: 703-714).

Protein accumulation disorders, including Alzheimer's disease (AD), frontotemporal dementia (FTD), Parkinson's disease (PD), Huntington's disease (HD), amyotrophic lateral sclerosis (ALS), and other dementias, are suspected to involve imbalances between protein production and protein clearance.

For example, synaptic pathology that disrupts neuronal connectivity has long been considered the key event in age-related disorders that 1) leads to cognitive deficits and 2) contributes to early, gradual changes that constitute risk factors for dementia.

Alzheimer's disease is characterized by a progressive inexorable loss of cognitive function. AD is characterized by two neuropathological hallmarks: excessive number of senile plaques in the cerebral cortex and subcortical gray matter which contains β-amyloid, and neurofibrillary tangles consisting of tau protein. In one study, researchers found that increased cathepsin B activity is associated with reduced β-amyloid accumulation and suggested using cilostazol, an agent shown to increase cathepsin B activity, for treating patients with A D (Park S Y, Lee H R, Lee W S, Shin H K, Kim H Y, Hong K W, et al. (2016) Cilostazol Modulates Autophagic Degradation of β-Amyloid Peptide via SIRT1-Coupled LKB1/AMPKα Signaling in Neuronal Cells. PLoS ONE 11(8): e0160620).

Heart failure is the leading cause of death in the developed world, and it represents a common endpoint for several diseases, including hypertension, coronary artery disease, and the cardiomyopathies. A lack of pathogenic commonality is underscored by the large number of mutations in different classes of cardiac proteins that have been linked to dilated and hypertrophic cardiomyopathy (HCM).

Amyloid oligomers are present in cardiomyocytes derived from human heart-failure subjects and in animal models of cardiomyopathy. From a study using cardiac stem cells cultured from explanted failing hearts, the authors suggested increasing cathepsin B activity as a way to protect heart cells (Gianfranceschi et al. (2016) "Critical role of lysosomes in the dysfunction of human Cardiac Stem Cells obtained from failing hearts" Int. J. Cardiol. 216:140-50).

There has been a line of studies suggesting that enhancement of cathepsin B activity is a compensatory event in response to protein accumulation stress. For example, in Gavilán et al., it was shown that cathepsin B increased in response to proteasome stress in young rats with brain-injected lactacystin (Gavilán et al., 2015). In Bendiske & Bahr, it was shown that cathepsin B increased in response to chloroquine-induced protein accumulation stress in hippocampal slices (Bendiske J, Bahr B A (2003) Lysosomal activation is a compensatory response against protein accumulation and synaptopathogenesis—An approach for slowing Alzheimer's disease? J Neuropathol Exp Neurol 62: 451-463).

Improved methods for treating protein accumulation diseases are needed.

SUMMARY OF THE INVENTION

The present invention provides new strategies for increasing cellular levels of active cathepsin B in order to enhance lysosomal activity, synaptic recovery, and cellular integrity in several tissue types. The present invention provides effective treatments for Alzheimer's disease, mild cognitive impairment (MCI), dementia, α-synucleinopathies, traumatic brain injury, cardiomyopathies, eye disease, and skin damage.

The present invention provides a method for treating a subject afflicted with i) Alzheimer's disease, ii) Mild Cognitive Impairment (MCI), or iii) dementia, comprising administering to the subject at least one compound that increases the level of active cathepsin B in brain cells of the subject, or a pharmaceutically acceptable salt or ester thereof, in an amount that is effective to treat the subject.

The present invention provides a method for treating a subject afflicted with cardiomyopathy comprising administering to the subject at least one compound that increases the level of active cathepsin B in heart cells of the subject, or a pharmaceutically acceptable salt or ester thereof, in an amount that is effective to treat the subject.

The present invention provides a method for treating a subject afflicted with i) a retinal disease, ii) an optic nerve disease, iii) retinal damage, or iv) optic nerve damage, comprising administering to the subject at least one compound that increases the level of active cathepsin B in eye cells of the subject, or a pharmaceutically acceptable salt or ester thereof, in an amount that is effective to treat the subject.

The present invention provides a method for treating a subject afflicted with traumatic brain injury (TBI), comprising administering to the subject and at least one compound that increases the level of active cathepsin B in brain cells of the subject, or a pharmaceutically acceptable salt or ester thereof, in an amount that is effective to treat the subject.

The present invention provides a method for treating a subject afflicted with skin damage, comprising administering to the subject at least one compound that increases the level of active cathepsin B in skin or hypodermis cells of the subject, or a pharmaceutically acceptable salt or ester thereof, in an amount that is effective to treat the subject.

The present invention provides a method for treating a subject afflicted with a protein accumulation disease or TBI, comprising orally administering to the subject at least one compound that increases the level of active cathepsin B in cells of the subject, or a pharmaceutically acceptable salt or ester thereof, in an amount that is effective to treat the subject.

The present invention provides a method for treating a subject afflicted with a protein accumulation disease or TBI, comprising administering to the subject an amount of a first compound and an amount of a second compound, wherein the first compound is PADK or a PADK analogue, or a pharmaceutically acceptable salt or ester thereof, and wherein the second compound is a flavonoid or a phenylalanyl proline compound, or a pharmaceutically acceptable salt or ester thereof.

The present invention provides a package comprising:
a. a first pharmaceutical composition comprising an amount of a first compound and a pharmaceutically acceptable carrier;
b. a second pharmaceutical composition comprising an amount of a second compound and a pharmaceutically acceptable carrier; and
c. instructions for use of the first and second pharmaceutical compositions together to treat a subject afflicted with a protein accumulation disease or TBI,
wherein the first compound is PADK or a PADK analogue, or a pharmaceutically acceptable salt or ester thereof, and wherein the second compound is a flavonoid or a phenylalanyl proline compound, or a pharmaceutically acceptable salt or ester thereof.

The present invention provides a therapeutic package for dispensing to, or for use in dispensing to, a subject afflicted with a protein accumulation disease or TBI, which comprises:
a. one or more unit doses, each such unit dose comprising:
i. an amount of a first compound and
ii. an amount of a second compound
wherein the respective amounts of the first compound and the second compound in said unit dose are effective, upon concomitant administration to said subject, to treat the subject, and
b. a finished pharmaceutical container therefor, said container containing said unit dose or unit doses, said container further containing or comprising labeling directing the use of said package in the treatment of said subject,
wherein the first compound is PADK or a PADK analogue, or a pharmaceutically acceptable salt or ester thereof, and wherein the second compound is a flavonoid or a phenylalanyl proline compound, or a pharmaceutically acceptable salt or ester thereof.

The present invention provides a pharmaceutical composition comprising an amount of a first compound and an amount of a second compound, wherein the first compound is PADK or a PADK analogue, or a pharmaceutically acceptable salt or ester thereof, and wherein the second compound is a flavonoid or a phenylalanyl proline compound, or a pharmaceutically acceptable salt or ester thereof.

The present invention provides a pharmaceutical composition in unit dosage form, useful in treating a subject afflicted with a protein accumulation disease or TBI, which comprises:
a. an amount of a first compound;
b. an amount of a second compound,
wherein the respective amounts of the first compound and the second compound in the composition are effective, upon concomitant administration to the subject of one or more of the unit dosage forms of the composition, to treat the subject, and
wherein the first compound is PADK or a PADK analogue, or a pharmaceutically acceptable salt or ester thereof, and wherein the second compound is a flavonoid or a phenylalanyl proline compound, or a pharmaceutically acceptable salt or ester thereof.

The present invention provides a pharmaceutical composition comprising an amount of a first compound for use in treating a subject afflicted with a protein accumulation disease or TBI as an add-on therapy or in combination with a second compound, wherein the first compound is PADK or a PADK analogue, or a pharmaceutically acceptable salt or ester thereof, and wherein the second compound is a flavonoid or a phenylalanyl proline compound, or a pharmaceutically acceptable salt or ester thereof.

The present invention provides a pharmaceutical composition comprising an amount of a first compound for use in treating a subject afflicted with a protein accumulation disease or TBI simultaneously, contemporaneously or concomitantly with a second compound, wherein the first compound is PADK or a PADK analogue, or a pharmaceutically acceptable salt or ester thereof, and wherein the second compound is a flavonoid or a phenylalanyl proline compound, or a pharmaceutically acceptable salt or ester thereof.

The present invention provides a first compound for use as an add-on therapy or in combination with a second compound in treating a subject afflicted with a protein accumulation disease or TBI, wherein the first compound is PADK or a PADK analogue, or a pharmaceutically acceptable salt or ester thereof, and wherein the second compound is a flavonoid or a phenylalanyl proline compound, or a pharmaceutically acceptable salt or ester thereof.

The present invention provides use of an amount of a first compound and an amount of a second compound in the preparation of a combination for treating a subject afflicted with a protein accumulation disease or TBI, wherein the first compound and the second compound are prepared to be administered simultaneously, contemporaneously or concomitantly, and wherein the first compound is PADK or a PADK analogue, or a pharmaceutically acceptable salt or ester thereof, and wherein the second compound is a flavonoid or a phenylalanyl proline compound, or a pharmaceutically acceptable salt or ester thereof.

The present invention provides use of an amount of a first compound in the manufacture of a medicament for treating a human patient afflicted with a protein accumulation disease or TBI, wherein the medicament is prepared for use as an add on therapy to or in combination with an amount of a second compound, wherein the amount of first compound and the amount of the second compound when taken together are more effective to treat the human patient than when each agent at the same amount is administered alone, and wherein the first compound is PADK or a PADK analogue, or a pharmaceutically acceptable salt or ester thereof, and wherein the second compound is a flavonoid or a phenylalanyl proline compound, or a pharmaceutically acceptable salt or ester thereof.

The present invention provides use of an amount of a first compound and an amount of a second compound in the manufacture of a medicament for treating a human patient afflicted with a protein accumulation disease or TBI, wherein the amount of the first compound and the amount of the second compound when taken together are more effective to treat the human patient than when each agent at the same amount is administered alone, and wherein the first compound is PADK or a PADK analogue, or a pharmaceutically acceptable salt or ester thereof, and wherein the second compound is a flavonoid or a phenylalanyl proline compound, or a pharmaceutically acceptable salt or ester thereof.

DETAILED DESCRIPTION OF THE INVENTION

Figure 1:
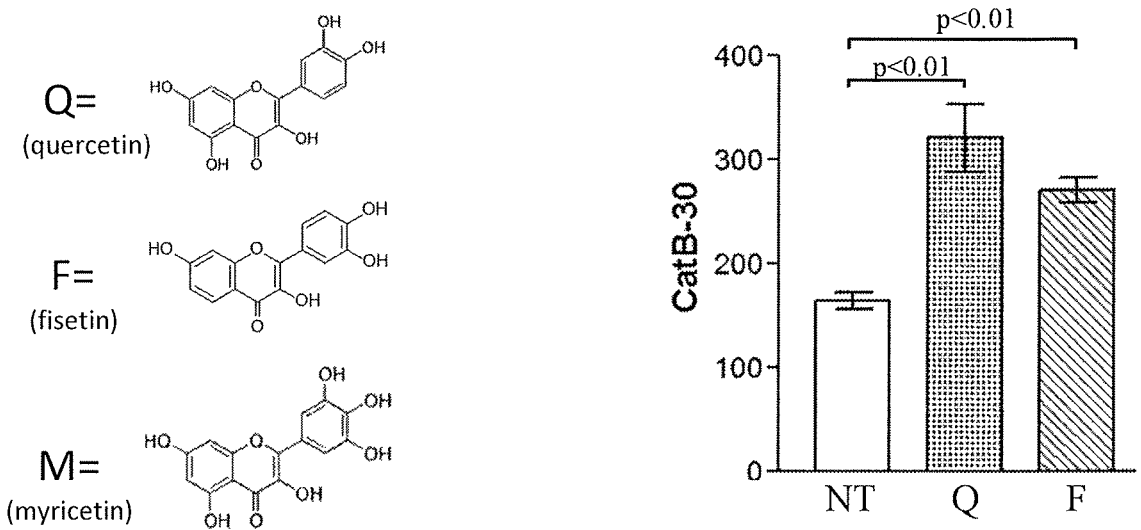
FIG. 1. Cathepsin B positive modulation by flavonols—members of the flavonoid class of polyphenolic compounds. Flavonols of quercetin (Q), fisetin (F), and myricetin (M) were applied daily to rodent hippocampal slice cultures. After two (2) days, non-treated (NT) and treated slices were harvested, homogenates were prepared, and equal protein aliquots were assessed by immunoblot to label the 30-kDa active form of cathepsin B (CatB-30). Statistically significant increases in cathepsin B were produced by 5-20 µM quercetin (1.96-fold) and by 5-30 µM fisetin (1.65-fold).

The present invention provides a method for treating a subject afflicted with i) Alzheimer's disease, ii) Mild Cognitive Impairment (MCI), or iii) dementia, comprising administering to the subject at least one compound that increases the level of active cathepsin B in brain cells of the subject, or a pharmaceutically acceptable salt or ester thereof, in an amount that is effective to treat the subject.

In some embodiments, the subject is afflicted with Alzheimer's disease.

In some embodiments, the subject is afflicted with MCI and a symptom of MCI in the subject is cognitive decline, and wherein treating the subject reduces the cognitive decline.

In some embodiments, the cognitive decline comprises memory loss.

In some embodiments, the subject is afflicted with dementia.

In some embodiments, there is a reduction in glucose use in the brain of the subject.

In some embodiments, there is a reduction in hippocampal volume in the brain of the subject.

In some embodiments, there is decreased expression of synaptophysin, AMPA-type glutamate receptor subunit GluR1, or an acetylcholinesterase (AChE) enzyme isoform, in the brain of the subject relative to i) a previous level of expression of synaptophysin, AMPA-type glutamate receptor subunit GluR1, or the AChE enzyme isoform in the brain of the subject, or ii) the level of expression of synaptophysin, AMPA-type glutamate receptor subunit GluR1, or the AChE enzyme isoform in the brains of subjects not afflicted with MCI.

In some embodiments, the subject has been diagnosed with Alzheimer's disease, MCI, or dementia using a cognitive test, a family history assessment, a blood test, a cerebrospinal fluid test (CSF), a neuronal connectivity scan, white matter integrity analysis, an magnetic resonance imaging (MRI) test of gray matter, an assessment of the microstructural integrity of axons and their surrounding myelin, a glucose metabolism assessment, a cortical thickness analysis, a multimodality biomarker assessment, genomic analysis, a sarcasm detection assessment, or any combination thereof.

In some embodiments, the brain cells are neurons or glial cells.

In some embodiments, the brain cells are neurons.

In some embodiments, the at least one compound induces an increase in the level of GluR1 in brain cells.

In some embodiments, the at least one compound induces an increase in the level of GluR1 in neurons.

The present invention provides a method for treating a subject afflicted with cardiomyopathy comprising administering to the subject at least one compound that increases the level of active cathepsin B in heart cells of the subject, or a pharmaceutically acceptable salt or ester thereof, in an amount that is effective to treat the subject.

In some embodiments, a symptom of the cardiomyopathy is peripheral edema, chest pain, an abnormal electrocardiogram, or myocardial dysfunction, and wherein treating the subject reduces the symptom.

In some embodiments, the cardiomyopathy is dilated cardiomyopathy, hypertrophic cardiomyopathy, or desmin-related cardiomyopathy.

In some embodiments, the dilated cardiomyopathy is idiopathic dilated cardiomyopathy.

In some embodiments, the at least one compound is administered in an amount that is effective to reduce the level of a cardiac amyloid oligomer in the heart cells of the subject.

In some embodiments, the cardiac amyloid oligomer is α-B-crystallin or an α-B-crystallin mutant.

In some embodiments, the heart cells are cardiac myocytes, intracoronary smooth muscle cells, intracoronary endothelial cells, or interstitial myofibroblasts.

In some embodiments, the heart cells are cardiac myocytes.

In some embodiments, the at least one compound increases the ratio between active cathepsin B and the proform precursor of cathepsin B in heart cells.

In some embodiments, the precursor of cathepsin B has a molecular weight of 80-110 kiloDaltons (kDa).

The present invention provides a method for treating a subject afflicted with i) a retinal disease, ii) an optic nerve disease, iii) retinal damage, or iv) optic nerve damage, comprising administering to the subject at least one compound that increases the level of active cathepsin B in eye cells of the subject, or a pharmaceutically acceptable salt or ester thereof, in an amount that is effective to treat the subject.

In some embodiments, the subject is afflicted with a retinal disease.

In some embodiments, the retinal disease is ischemic retinopathy, diabetic retinopathy, macular degeneration, or retinitis pigmentosa.

In some embodiments, the retinal disease is macular degeneration.

In some embodiments, the macular degeneration is age-related macular degeneration.

In some embodiments, the age-related macular degeneration is wet age-related macular degeneration.

In some embodiments, the age-related macular degeneration is dry age-related macular degeneration.

In some embodiments, the subject is afflicted with an optic nerve disease.

In some embodiments, the optic nerve disease is optic neuropathy.

In some embodiments, the optic neuropathy is ischemic optic neuropathy or glaucoma.

In some embodiments, the subject is afflicted with retinal damage.

In some embodiments, the retinal damage is iatrogenic retinopathy, a retinal tear, or a retinal hole.

In some embodiments, the at least one compound is administered in an amount that is effective to reduce the level of amyloid μ (Aβ), vitronectin, amyloid P, orapolipoprotein E in the eye cells of the subject.

In some embodiments, the eye cells are photoreceptor cells.

In some embodiments, the photoreceptor cells are cone cells.

In some embodiments, the photoreceptor cells are rod cells.

The present invention provides a method for treating a subject afflicted with traumatic brain injury (TBI), comprising administering to the subject at least one compound that increases the level of active cathepsin B in brain cells of the subject, or a pharmaceutically acceptable salt or ester thereof, in an amount that is effective to treat the subject.

In some embodiments, the TBI was sustained by the subject while participating in a contact sport, and wherein the contact sport is boxing, martial arts, mixed martial arts, football, or rugby.

In some embodiments, the TBI is from an explosion shockwave.

In some embodiments, the brain cells are neurons or glial cells.

In some embodiments, the brain cells are neurons, and the at least one compound is administered in an amount that is effective to reduce the level of at least one accumulated protein that is potentially pathogenic from the neurons of the subject.

In some embodiments, the at least one compound is administered in an amount that is effective to reduce the level of at least one accumulated protein that is potentially pathogenic from the axonal bulbs or varicosities of neurons of the subject.

In some embodiments, the at least one accumulated protein is neurofilament protein, amyloid precursor protein (APP), beta-site APP cleaving enzyme (BACE), presenilin-1 (PS1), Aβ, tau protein, α-synuclein, or any combination thereof.

The present invention provides a method for treating a subject afflicted with skin damage, comprising administering to the subject at least one compound that increases the level of active cathepsin B in skin or hypodermis cells of the subject, or a pharmaceutically acceptable salt or ester thereof, in an amount that is effective to treat the subject.

In some embodiments, the skin damage is a sunburn.

In some embodiments, the skin damage is dermal photodamage.

In some embodiments, the dermal photodamage is dermal photoaging.

In some embodiments, the dermal photodamage is from solar UV-radiation.

In some embodiments, the UV-radiation is UVA-radiation.

In some embodiments, the skin damage is a skin wound.

In some embodiments, the skin wound is skin laceration.

In some embodiments, the skin wound is a skin puncture.

In some embodiments, the skin wound is a skin abrasion.

In some embodiments, the skin wound is a skin burn.

In some embodiments, the at least one compound increases the level of active cathepsin B in skin cells of the subject.

In some embodiments, the skin cells are keratinocytes, Merkel cells, melanocytes, or Langerhans cells.

In some embodiments, the at least one compound increases the level of active cathepsin B in hypodermis cells of the subject.

In some embodiments, the hypodermis cells are fibroblasts, macrophages, or adipocytes.

In some embodiments, the at least one compound is administered to the subject parenterally, by inhalation, intranasally, topically, subcutaneously, intramuscularly, rectally or by intrapulmonary injection.

In some embodiments, the at least one compound is orally administered to the subject.

In some embodiments, the at least one compound is orally administered to the subject in a pharmaceutically acceptable carrier that has a high oil content or a high protein content.

In some embodiments, the pharmaceutically acceptable carrier has an oil content of about 25, 30, 35, 40, 45, 50, 55, 60, 65, 70, 75, 80, 85, 90, 95, 99, or 100% (w/w).

In some embodiments, the pharmaceutically acceptable carrier has a protein content of about 25, 30, 35, 40, 45, 50, 55, 60, 65, 70, 75, 80, 85, 90, 95, 99, or 100% (w/w).

In some embodiments, the pharmaceutically acceptable carrier comprises animal oil.

In some embodiments, the animal oil is fish oil.

In some embodiments, the pharmaceutically acceptable carrier comprises vegetable oil.

In some embodiments, the pharmaceutically acceptable carrier comprises peanut butter.

In some embodiments, the pharmaceutically acceptable carrier is peanut butter.

The present invention provides a method for treating a subject afflicted with a protein accumulation disease or TBI, comprising orally administering to the subject at least one compound that increases the level of active cathepsin B in cells of the subject, or a pharmaceutically acceptable salt or ester thereof, in an amount that is effective to treat the subject.

In some embodiments, the subject is afflicted with a protein accumulation disease.

In some embodiments, the protein accumulation disease is
i) a brain protein accumulation disease, and the cells are brain cells;
ii) cardiomyopathy, and the cells are heart cells;
iii) macular degeneration, and the cells are eye cells; or
iv) skin damage, and the cells are skin cells or hypodermis cells.

In some embodiments, the protein accumulation disease is a brain protein accumulation disease and the cells are brain cells.

In some embodiments, the brain protein accumulation disease is Alzheimer's disease, Huntington's disease, α-synucleinopathy, MCI, dementia, or amyotrophic lateral sclerosis.

In some embodiments, the brain protein accumulation disease is α-synucleinopathy.

In some embodiments, the α-synucleinopathy is Parkinson's disease.

In some embodiments, the brain protein accumulation disease is MCI.

In some embodiments, the brain protein accumulation disease is dementia.

In some embodiments, the dementia is early dementia.

In some embodiments, the dementia is intermediate dementia.

In some embodiments, the dementia is late dementia.

In some embodiments, the brain protein accumulation disease is
Alzheimer's disease.

In some embodiments, the brain protein accumulation disease is Huntington's disease.

In some embodiments, the brain protein accumulation disease is amyotrophic lateral sclerosis.

In some embodiments, the subject has been diagnosed with the brain protein accumulation disease using a cognitive test, a family history assessment, a blood test, a cerebrospinal fluid test (CSF), a neuronal connectivity scan, white matter integrity analysis, an magnetic resonance imaging (MRI) test of gray matter, an assessment of the microstructural integrity of axons and their surrounding myelin, a glucose metabolism assessment, a cortical thickness analysis, a multimodality biomarker assessment, genomic analysis, a sarcasm detection assessment, or any combination thereof.

In some embodiments, the brain cells are neurons or glial cells.

In some embodiments, the brain cells are neurons.

In some embodiments, the at least one compound induces an increase in the level of GluR1 in brain cells.

In some embodiments, the at least one compound induces an increase in the level of GluR1 in neurons.

In some embodiments, there is a reduction in glucose use in the brain of the subject.

In some embodiments, hippocampal volume in the brain of the subject is reduced.

In some embodiments, there is decreased expression of synaptophysin, AMPA-type glutamate receptor subunit GluR1, or an acetylcholinesterase (AChE) enzyme isoform, in the brain of the subject relative to i) a previous level of expression of synaptophysin, AMPA-type glutamate receptor subunit GluR1, or the AChE enzyme isoform in the brain of the subject, or ii) the level of expression of synaptophysin, AMPA-type glutamate receptor subunit GluR1, or the AChE enzyme isoform in the brains of subjects not afflicted with the brain protein accumulation disease.

In some embodiments, the subject is afflicted with TBI and the cells are brain cells.

In some embodiments, the active cathepsin B has a molecular weight of about 25-30 kDa.

In some embodiments, the subject is a mammalian subject.

In some embodiments, the mammalian subject is a human subject.

In some embodiments, the human subject is at least about 20, 25, 30, 35, 40, 45, 50, 55, 60, 65, 70, 75, 80, or 85 years of age.

In some embodiments, the at least one compound is orally administered to the subject in a pharmaceutically acceptable carrier.

In some embodiments, the pharmaceutically acceptable carrier has a high oil content.

In some embodiments, the pharmaceutically acceptable carrier has an oil content of about 25, 30, 35, 40, 45, 50, 55, 60, 65, 70, 75, 80, 85, 90, 95, 99, or 100% (w/w).

In some embodiments, the pharmaceutically acceptable carrier has a high protein content.

In some embodiments, the pharmaceutically acceptable carrier has a protein content of about 25, 30, 35, 40, 45, 50, 55, 60, 65, 70, 75, 80, 85, 90, 95, 99, or 100% (w/w).

In some embodiments, the pharmaceutically acceptable carrier comprises animal oil.

In some embodiments, the animal oil is fish oil.

In some embodiments, the pharmaceutically acceptable carrier comprises vegetable oil.

In some embodiments, the pharmaceutically acceptable carrier comprises peanut butter.

In some embodiments, the pharmaceutically acceptable carrier is peanut butter.

In some embodiments, the at least one compound is a compound having the structure:

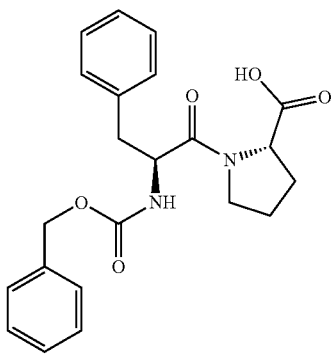 [SMILES: O=C(N[C@@H](Cc1ccccc1)C(=O)N1CCC[C@H]1C(=O)O)OCc1ccccc1]

or an analogue thereof, or a pharmaceutically acceptable salt or ester thereof.

In some embodiments, the at least one compound is Z-phenylalanyl-alanyl-diazomethylketone (PADK) or a PADK analogue, or a pharmaceutically acceptable salt or ester thereof.

In some embodiments, the at least one compound is a PADK analogue.

In some embodiments, the PADK analogue is Z-L-phenylalanyl-D-alanyl-diazomethylketone (PdADK) Z-D-phenylalanyl-L-alanyl-diazomethylketone (dPADK) or Z-D-phenylalanyl-D-alanyl-diazomethylketone (dPdADK).

In some embodiments, the PADK analogue is Z-phenylalanyl-phenylalanyl-diazomethylketone (PPDK), or a pharmaceutically acceptable salt or ester thereof.

In some embodiments, the PADK analogue is Z-L-phenylalanyl-D-phenylalanyl-diazomethylketone (PdPDK) Z-D-phenylalanyl-L-phenylalanyl-diazomethylketone (dPPDK) or Z-D-phenylalanyl-D-phenylalanyl-diazomethylketone (dPdPDK).

In some embodiments, the first or second amino acid chiral carbon of the PADK analogue is methylated, or wherein both the first and second amino acid chiral carbon of the PADK analogue is methylated.

In some embodiments, the PADK analogue has the structure:

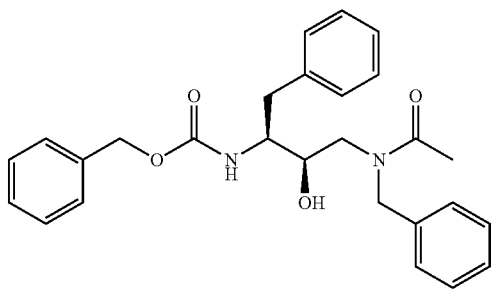 [SMILES: CC(=O)N(Cc1ccccc1)C[C@@H](O)[C@H](Cc1ccccc1)NC(=O)OCc1ccccc1]

or a pharmaceutically acceptable salt or ester thereof.

In some embodiments, the PADK analogue has the structure:

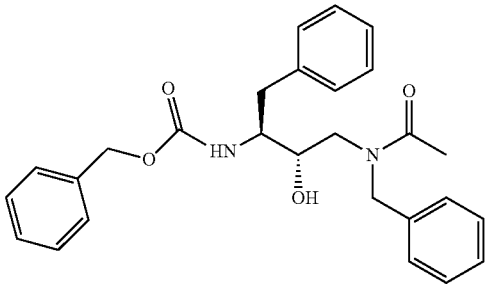 [SMILES: CC(=O)N(Cc1ccccc1)C[C@H](O)[C@H](Cc1ccccc1)NC(=O)OCc1ccccc1]

or a pharmaceutically acceptable salt or ester thereof.

In some embodiments, the PADK analogue has the structure:

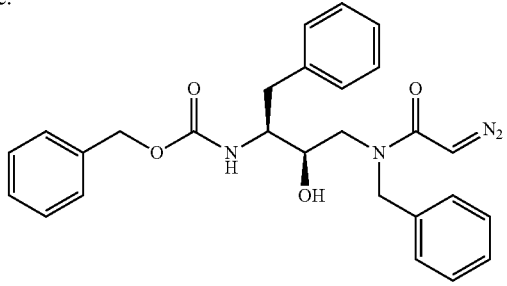

or a pharmaceutically acceptable salt or ester thereof.

In some embodiments, the at least one compound is a flavonoid.

In some embodiments, the flavonoid comprises one or more flavonols.

In some embodiments, the one or more flavonols comprise one or more of quercetin, fisetin, and myricetin, or an analogue thereof.

In some embodiments, the one or more flavonols is quercetin or a quercetin analogue.

In some embodiments, the one or more flavonols is fisetin or a fisetin analogue.

In some embodiments, the one or more flavonols is myricetin or a myricetin analogue.

In some embodiments, the method comprises administering to the subject a combination of two, three, four, or more of:
i) a compound having the structure:

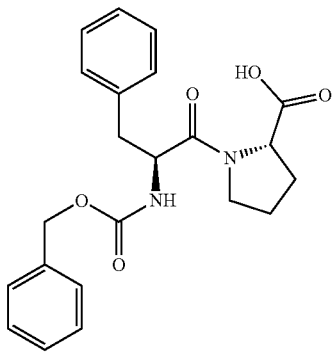 [SMILES: O=C(N[C@@H](Cc1ccccc1)C(=O)N1CCC[C@H]1C(=O)O)OCc1ccccc1]

or an analogue thereof, or a pharmaceutically acceptable salt or ester thereof;
ii) PADK or a PADK analogue, or a pharmaceutically acceptable salt or ester thereof;

iii) PPDK or a pharmaceutically acceptable salt or ester thereof;
iv) a PADK analogue having the structure:

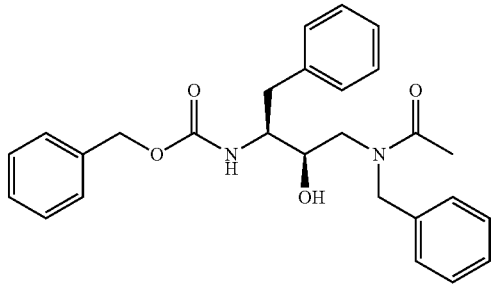 [SMILES: CC(=O)N(Cc1ccccc1)C[C@@H](O)[C@H](Cc1ccccc1)NC(=O)OCc1ccccc1]

or a pharmaceutically acceptable salt or ester thereof;
v) a PADK analogue having the structure:

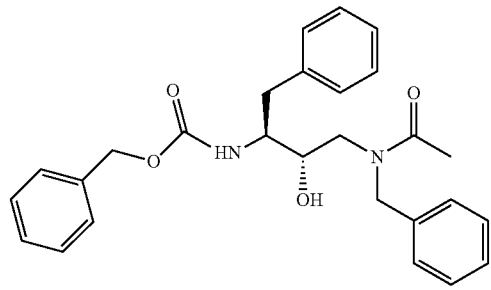 [SMILES: CC(=O)N(Cc1ccccc1)C[C@H](O)[C@H](Cc1ccccc1)NC(=O)OCc1ccccc1]

or a pharmaceutically acceptable salt or ester thereof;
vi) a PADK analogue having the structure:

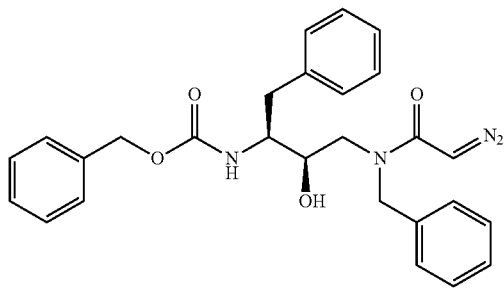

or a pharmaceutically acceptable salt or ester thereof; or
vii) a flavonoid,
each in an amount that when administered together is effective to treat the subject, or increase the level of active cathepsin B in brain, heart, eye, or skin cells of the subject.

In some embodiments, the method comprises administering to the subject a combination of a flavonoid and PADK or a PADK analogue, wherein the flavonoid is quercetin or a quercetin analogue.

In some embodiments, the method comprises administering to the subject a combination of a flavonoid and PADK or a PADK analogue, wherein the flavonoid is fisetin or a fisetin analogue.

In some embodiments, the method comprises administering to the subject a combination of a flavonoid and PADK or a PADK analogue, wherein the flavonoid is myricetin or a myricetin analogue.

In some embodiments, the method comprises administering to the subject a combination of PADK or a PADK analogue and a compound having the structure:

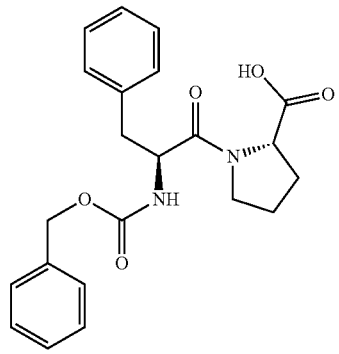 [SMILES: O=C(N[C@@H](Cc1ccccc1)C(=O)N1CCC[C@H]1C(=O)O)OCc1ccccc1]

or an analogue thereof, or a pharmaceutically acceptable salt or ester thereof.

In some embodiments, a combination of the compounds wherein one of the compounds is a flavonoid is more effective to treat the subject than each compound when taken alone.

In some embodiments, a lower amount of the compound in combination with a flavonoid is as effective to treat the subject as a higher amount of the same compound when taken alone.

In some embodiments, the at least one compound or combination increases the level of active cathepsin B in brain, heart, or skin cells at least about 1.5, 2, 3, 4, 5, 6, 7, 8, 9, 10, 11, 12, 14, 14, or 15-fold.

In some embodiments, the at least one compound or combination increases cathepsin B trafficking in brain, heart, or skin cells.

In some embodiments, the at least one compound or combination increases cathepsin B maturation in brain, heart, or skin cells.

The present invention provides a composition for treating a subject afflicted with a protein accumulation disease or TBI, comprising at least one compound or combination, disclosed herein, and a pharmaceutically acceptable carrier.

The present invention provides a method for treating a subject afflicted with a protein accumulation disease or TBI, comprising administering to the subject an amount of a first compound and an amount of a second compound, wherein the first compound is PADK or a PADK analogue, or a pharmaceutically acceptable salt or ester thereof, and wherein the second compound is a flavonoid or a phenylalanyl proline compound, or a pharmaceutically acceptable salt or ester thereof.

In some embodiments, the method comprises periodically administering to the subject the amount of the first compound and the amount of the second compound, wherein the amount of the first compound and the amount of the second compound when taken together is more effective to treat the subject than when each compound at the same respective amount is administered alone.

In some embodiments, each of the amount of the first compound when taken alone, and the amount of the second compound when taken alone is effective to treat the subject.

In some embodiments, either the amount of the first compound when taken alone, the amount of the second compound when taken alone, or each such amount when taken alone is not effective to treat the subject.

In some embodiments, the subject is a human patient.

In some embodiments, the first compound is:

i) a PADK analogue having the structure:

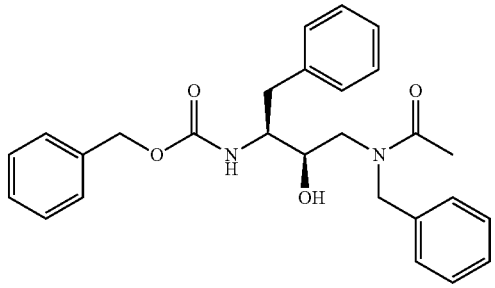 [SMILES: CC(=O)N(Cc1ccccc1)C[C@@H](O)[C@H](Cc1ccccc1)NC(=O)OCc1ccccc1]

or a pharmaceutically acceptable salt or ester thereof;

ii) a PADK analogue having the structure:

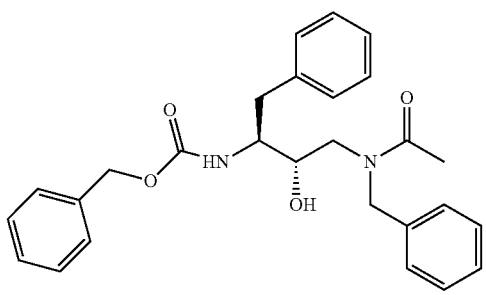 [SMILES: CC(=O)N(Cc1ccccc1)C[C@H](O)[C@H](Cc1ccccc1)NC(=O)OCc1ccccc1]

or a pharmaceutically acceptable salt or ester thereof; or iii) a PADK analogue having the structure:

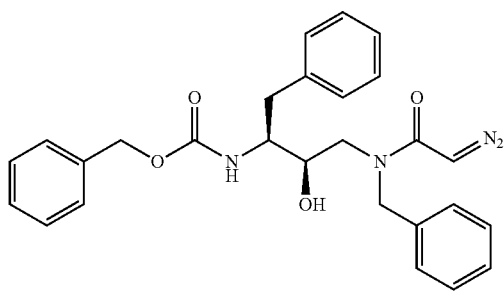

or a pharmaceutically acceptable salt or ester thereof.

In some embodiments, the second compound is one or more of quercetin, a quercetin analogue, fisetin, a fisetin analogue, myricetin, a myricetin analogue, or a phenylalanyl proline compound having the structure:

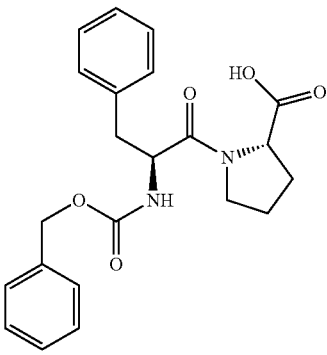 [SMILES: O=C(N[C@@H](Cc1ccccc1)C(=O)N1CCC[C@H]1C(=O)O)OCc1ccccc1]

or an analogue thereof.

The present invention provides a package comprising:
a. a first pharmaceutical composition comprising an amount of a first compound and a pharmaceutically acceptable carrier;
b. a second pharmaceutical composition comprising an amount of a second compound and a pharmaceutically acceptable carrier; and
c. instructions for use of the first and second pharmaceutical compositions together to treat a subject afflicted with a protein accumulation disease or TBI, wherein the first compound is PADK or a PADK analogue, or a pharmaceutically acceptable salt or ester thereof, and wherein the second compound is a flavonoid or a phenylalanyl proline compound, or a pharmaceutically acceptable salt or ester thereof.

In some embodiments, the first pharmaceutical composition, the second pharmaceutical composition, or both the first and the second pharmaceutical compositions are in an aerosol, an inhalable powder, an injectable, a liquid, a solid, a capsule or a tablet form.

In some embodiments, the first pharmaceutical composition, the second pharmaceutical composition, or both the first and the second pharmaceutical compositions are in a liquid or a solid form.

In some embodiments, the first pharmaceutical composition, the second pharmaceutical composition, or both the first and the second pharmaceutical compositions are in capsule form or in tablet form.

In some embodiments, the tablets are coated with a coating which inhibits oxygen from contacting the core.

In some embodiments, the coating comprises a cellulosic polymer, a detackifier, a gloss enhancer, or pigment.

In some embodiments, the first pharmaceutical composition and/or the second pharmaceutical composition is stable and free of an alkalinizing agent or an oxidation reducing agent.

In some embodiments, the first pharmaceutical composition and/or the second pharmaceutical composition is free of an alkalinizing agent and free of an oxidation reducing agent.

In some embodiments, the first pharmaceutical composition and/or the second pharmaceutical composition is stable and free of disintegrant.

In some embodiments, the package further comprises a desiccant. In some embodiments, the desiccant is silica gel.

In some embodiments, the first pharmaceutical composition and/or the second pharmaceutical composition is stable and has a moisture content of no more than 4%.

In some embodiments, the package is a sealed packaging having a moisture permeability of not more than 15 mg/day per liter. In some embodiments, the sealed package is a blister pack in which the maximum moisture permeability is no more than 0.005 mg/day. In some embodiments, the sealed package is a bottle and/or comprises an HDPE bottle. In some embodiments, the bottle is closed with a heat induction liner. In some embodiments, the sealed package comprises an oxygen absorbing agent. In some embodiments, the oxygen absorbing agent is iron.

In some embodiments, the amount of the first compound and the amount of the second compound are prepared to be administered simultaneously, contemporaneously or concomitantly.

The present invention provides a therapeutic package for dispensing to, or for use in dispensing to, a subject afflicted with a protein accumulation disease or TBI, which comprises:
  a. one or more unit doses, each such unit dose comprising:
    i. an amount of a first compound and
    ii. an amount of a second compound
    wherein the respective amounts of the first compound and the second compound in said unit dose are effective, upon concomitant administration to said subject, to treat the subject, and
  b. a finished pharmaceutical container therefor, said container containing said unit dose or unit doses, said container further containing or comprising labeling directing the use of said package in the treatment of said subject,
wherein the first compound is PADK or a PADK analogue, or a pharmaceutically acceptable salt or ester thereof, and wherein the second compound is a flavonoid or a phenylalanyl proline compound, or a pharmaceutically acceptable salt or ester thereof.

In some embodiments, the respective amounts of the first compound and the second compound in the unit dose when taken together is more effective to treat the subject than when compared to the administration of the first compound in the absence of the second compound or the administration of the second compound in the absence of the first compound.

The present invention provides a pharmaceutical composition comprising an amount of a first compound and an amount of a second compound, wherein the first compound is PADK or a PADK analogue, or a pharmaceutically acceptable salt or ester thereof, and wherein the second compound is a flavonoid or a phenylalanyl proline compound, or a pharmaceutically acceptable salt or ester thereof.

In some embodiments, the pharmaceutical composition consists essentially of the amount of the first compound and the amount of the second compound.

In some embodiments, the pharmaceutical composition is for use in treating a subject afflicted with a protein accumulation disease or TBI, wherein the first compound and the second compound are prepared to be administered simultaneously, contemporaneously or concomitantly.

In some embodiments, the pharmaceutical composition is in an aerosol, an inhalable powder, an injectable, a liquid, a solid, a capsule or a tablet form. In some embodiments, the tablets are coated with a coating which inhibits oxygen from contacting the core. In some embodiments, the coating comprises a cellulosic polymer, a detackifier, a gloss enhancer, or pigment.

In some embodiments, the pharmaceutical composition is free of an alkalinizing agent or an oxidation reducing agent.

In some embodiments, the pharmaceutical composition is free of an alkalinizing agent and free of an oxidation reducing agent.

In some embodiments, the pharmaceutical composition is stable and free of disintegrant.

The present invention provides a pharmaceutical composition in unit dosage form, useful in treating a subject afflicted with a protein accumulation disease or TBI, which comprises:
  c. an amount of a first compound;
  d. an amount of a second compound,
wherein the respective amounts of the first compound and the second compound in the composition are effective, upon concomitant administration to the subject of one or more of the unit dosage forms of the composition, to treat the subject, and
wherein the first compound is PADK or a PADK analogue, or a pharmaceutically acceptable salt or ester thereof, and wherein the second compound is a flavonoid or a phenylalanyl proline compound, or a pharmaceutically acceptable salt or ester thereof.

In some embodiments, the respective amounts of the first compound and the second compound in the unit dose when taken together is more effective to treat the subject than when compared to the administration of the first compound in the absence of the second compound or the administration of the second compound in the absence of the first compound.

The present invention provides a pharmaceutical composition comprising an amount of a first compound for use in treating a subject afflicted with a protein accumulation disease or TBI as an add-on therapy or in combination with a second compound, wherein the first compound is PADK or a PADK analogue, or a pharmaceutically acceptable salt or ester thereof, and wherein the second compound is a flavonoid or a phenylalanyl proline compound, or a pharmaceutically acceptable salt or ester thereof.

The present invention provides a pharmaceutical composition comprising an amount of a first compound for use in treating a subject afflicted with a protein accumulation disease or TBI simultaneously, contemporaneously or concomitantly with a second compound, wherein the first compound is PADK or a PADK analogue, or a pharmaceutically acceptable salt or ester thereof, and wherein the second compound is a flavonoid or a phenylalanyl proline compound, or a pharmaceutically acceptable salt or ester thereof.

The present invention provides a first compound for use as an add-on therapy or in combination with a second compound in treating a subject afflicted with a protein accumulation disease or TBI, wherein the first compound is PADK or a PADK analogue, or a pharmaceutically acceptable salt or ester thereof, and wherein the second compound is a flavonoid or a phenylalanyl proline compound, or a pharmaceutically acceptable salt or ester thereof.

The present invention provides use of an amount of a first compound and an amount of a second compound in the preparation of a combination for treating a subject afflicted with a protein accumulation disease or TBI, wherein the first compound and the second compound are prepared to be administered simultaneously, contemporaneously or concomitantly, and wherein the first compound is PADK or a PADK analogue, or a pharmaceutically acceptable salt or ester thereof, and wherein the second compound is a flavonoid or a phenylalanyl proline compound, or a pharmaceutically acceptable salt or ester thereof The present invention provides use of an amount of a first compound in the manufacture of a medicament for treating a human patient afflicted with a protein accumulation disease or TBI, wherein the medicament is prepared for use as an add on therapy to or in combination with an amount of a second compound, wherein the amount of first compound and the amount of the second compound when taken together are more effective to treat the human patient than when each agent at the same amount is administered alone, and wherein the first compound is PADK or a PADK analogue, or a pharmaceutically acceptable salt or ester thereof, and wherein the second compound is a flavonoid or a phenylalanyl proline compound, or a pharmaceutically acceptable salt or ester thereof.

The present invention provides use of an amount of a first compound and an amount of a second compound in the manufacture of a medicament for treating a human patient afflicted with a protein accumulation disease or TBI, wherein the amount of the first compound and the amount of the second compound when taken together are more effective to treat the human patient than when each agent at the same amount is administered alone, and wherein the first compound is PADK or a PADK analogue, or a pharmaceutically acceptable salt or ester thereof, and wherein the second compound is a flavonoid or a phenylalanyl proline compound, or a pharmaceutically acceptable salt or ester thereof.

In some embodiments, the amount of the first compound and the amount of the second compound when taken together is effective to reduce a symptom of a protein accumulation disease or TBI in the human patient.

In some embodiments, the at least one compound is a phenylalanyl proline compound. One such phenylalanyl proline compound is N-carbobenzoxy-L-phenylalanyl-L-proline (Z-Phe-Pro-OH), which has the structure:

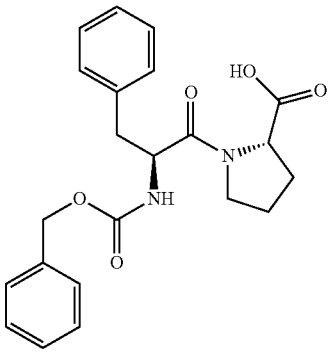 [SMILES: O=C(N[C@@H](Cc1ccccc1)C(=O)N1CCC[C@H]1C(=O)O)OCc1ccccc1]

or a pharmaceutically acceptable salt or ester thereof. Z-Phe-Pro-OH is commercially available from ChemDiv Inc. (San Diego, Calif., USA).

In some embodiments, the at least one compound is a flavonoid, such as one or more flavonols, where the flavonol may be quercetin, fisetin, or myricetin, or an analogue thereof. Flavonols, such as quercetin, fisetin, and myricetin, are commercially available from Sigma-Aldrich Co. LLC (St. Louis, Mo., USA).

In some embodiments, the at least one compound is Z-phenylalanyl-alanyl-diazomethylketone (PADK) or a PADK analogue, or a pharmaceutically acceptable salt or ester thereof. PADK may also be referred to as Z-Phe-Ala-diazomethylketone. The CAS Number for PADK is 71732-53-1. PADK is commercially available from Bachem Americas, Inc. (N-1040; Torrance, Calif., USA).

In some embodiments, the PADK analogue is Z-phenylalanyl-phenylalanyl-diazomethylketone (PPDK), or a pharmaceutically acceptable salt or ester thereof. PPDK is also known as Z-Phe-Phe-diazomethylketone. The CAS Number for PPDK is 65178-14-5. PPDK is commercially available from Bachem Americas, Inc. (N-1045; Torrance, Calif., USA).

The structures for PADK and PPDK are:

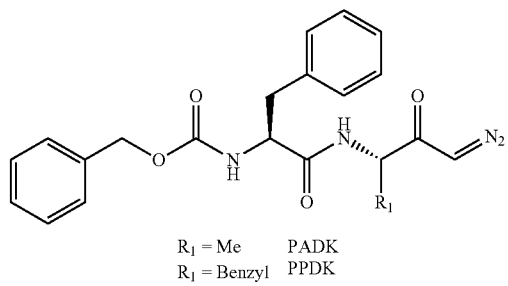

R₁ = Me    PADK
R₁ = Benzyl    PPDK

The structure for PADK is:

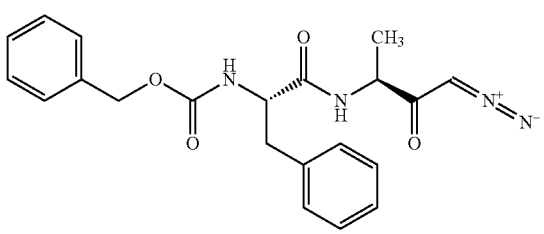

The structure for PPDK is:

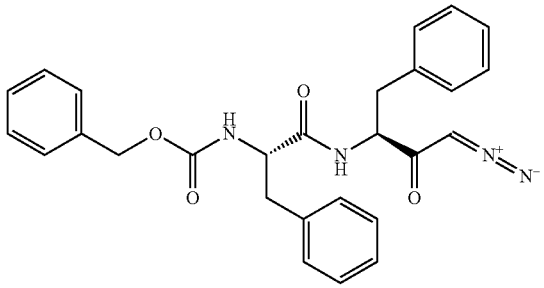 [SMILES: [N-]=[N+]=CC(=O)[C@H](Cc1ccccc1)NC(=O)[C@H](Cc1ccccc1)NC(=O)OCc1ccccc1]

In some embodiments, the at least one compound has the structure:

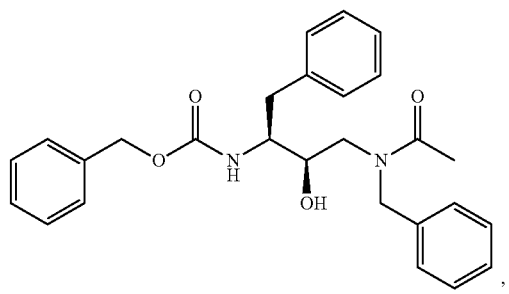

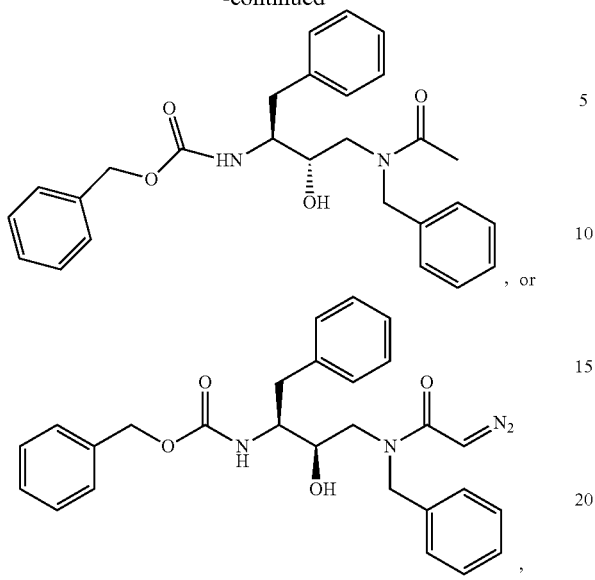

or a pharmaceutically acceptable salt or ester thereof. Methods for synthesizing these compounds are described in Viswanathan et al (2012) "Nonpeptidic Lysosomal Modulators Derived from Z-Phe-Ala-Diazomethylketone for Treating Protein Accumulation Diseases" ACS Med. Chem. Lett., 3, 920-924, the entire contents of which are incorporated herein by reference. Additionally, Synthesis Schemes for these compounds are provided below.

Synthesis Scheme I

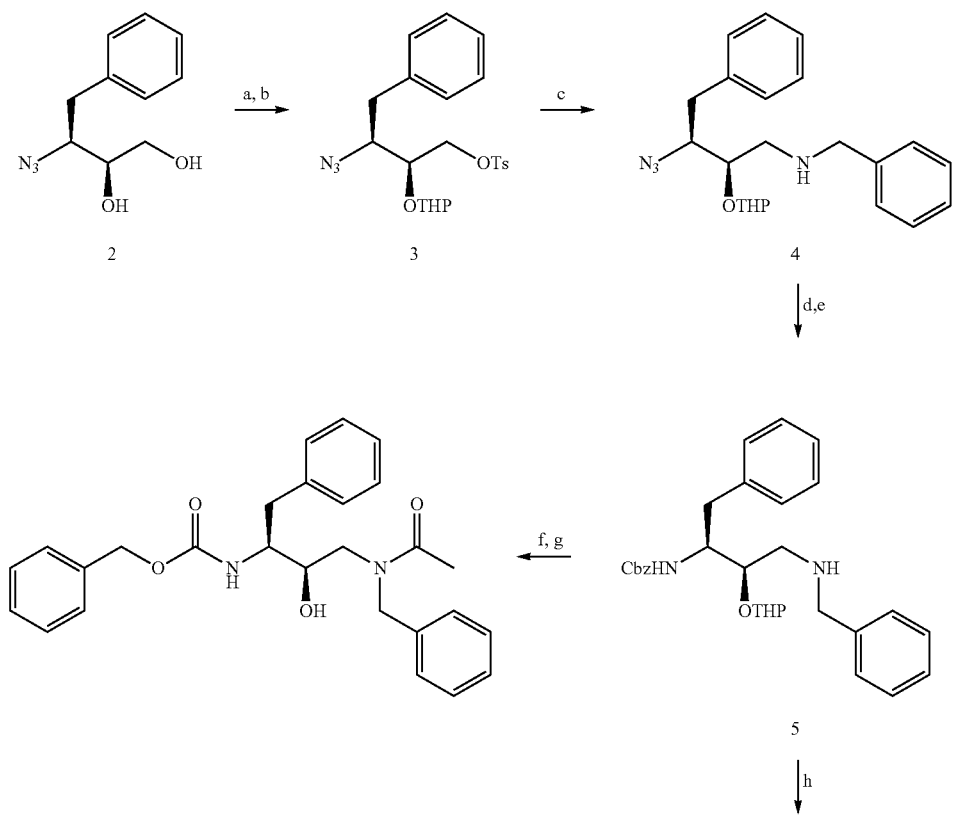

23

-continued

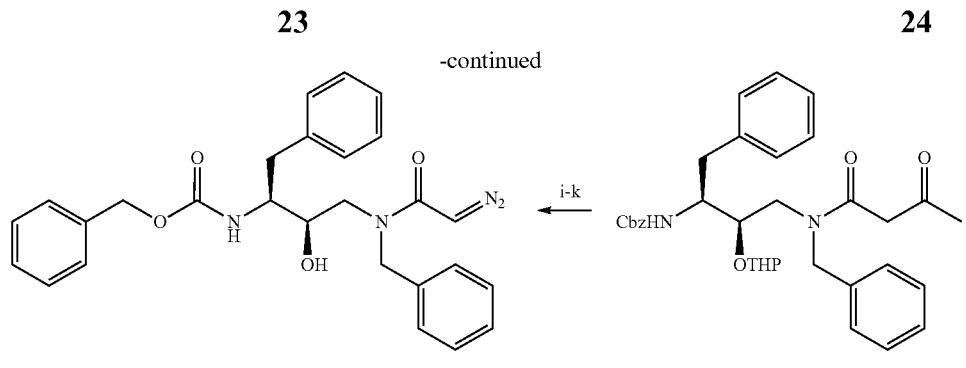

Reagents and conditions: (a) TsCl, pyridine; (b) dihydropyran, PPTS, CH2Cl2; (c) benzylamine, THF, reflux; (d) H2, Pd/C, EtOH; (e) PhCH2OC(O)Cl, NaHCO3; (f) PPTS, EtOH, 60° C.; (g) Ac2O, Et3N, DMAP, THF; (h) diketene, EtOH; (i) TsN3, DBU, AcCN; (j) LiOH/H2O; (k) PPTS, EtOH, 40° C.

24

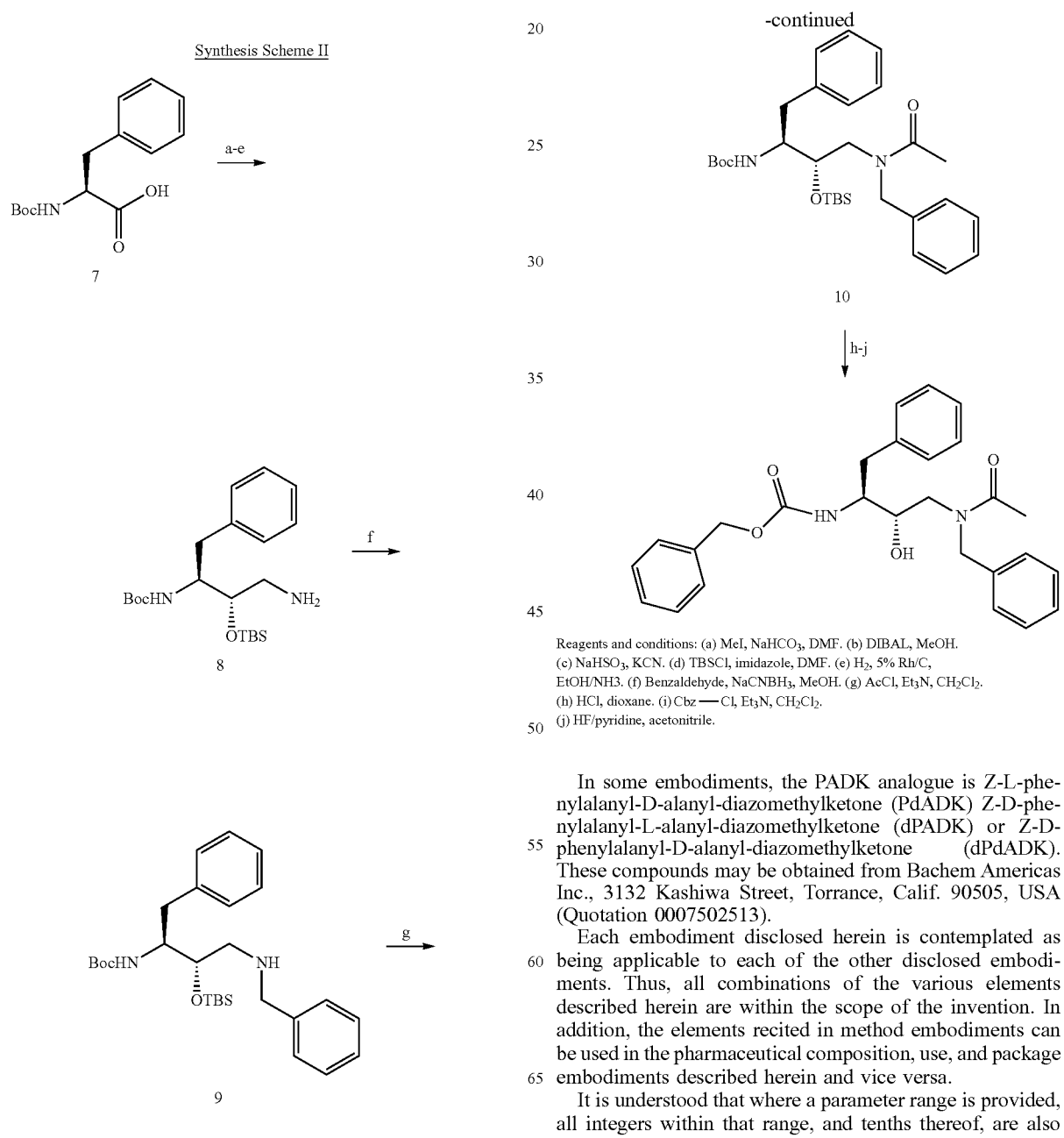

Reagents and conditions: (a) MeI, NaHCO3, DMF. (b) DIBAL, MeOH. (c) NaHSO3, KCN. (d) TBSCl, imidazole, DMF. (e) H2, 5% Rh/C, EtOH/NH3. (f) Benzaldehyde, NaCNBH3, MeOH. (g) AcCl, Et3N, CH2Cl2. (h) HCl, dioxane. (i) Cbz—Cl, Et3N, CH2Cl2. (j) HF/pyridine, acetonitrile.

In some embodiments, the PADK analogue is Z-L-phenylalanyl-D-alanyl-diazomethylketone (PdADK) Z-D-phenylalanyl-L-alanyl-diazomethylketone (dPADK) or Z-D-phenylalanyl-D-alanyl-diazomethylketone (dPdADK). These compounds may be obtained from Bachem Americas Inc., 3132 Kashiwa Street, Torrance, Calif. 90505, USA (Quotation 0007502513).

Each embodiment disclosed herein is contemplated as being applicable to each of the other disclosed embodiments. Thus, all combinations of the various elements described herein are within the scope of the invention. In addition, the elements recited in method embodiments can be used in the pharmaceutical composition, use, and package embodiments described herein and vice versa.

It is understood that where a parameter range is provided, all integers within that range, and tenths thereof, are also provided by the invention. For example, "0.2-5 mg/kg/day" is a disclosure of 0.2 mg/kg/day, 0.3 mg/kg/day, 0.4 mg/kg/day, 0.5 mg/kg/day, 0.6 mg/kg/day etc. up to 5.0 mg/kg/day.

Terms

Unless otherwise defined, all technical and scientific terms used herein have the same meaning as commonly understood by a person of ordinary skill in the art to which this invention belongs.

As used herein, and unless stated otherwise or required otherwise by context, each of the following terms shall have the definition set forth below.

As used herein, "about" in the context of a numerical value or range means±10% of the numerical value or range recited or claimed, unless the context requires a more limited range.

As used herein, "treating" means slowing, stopping, or reversing the progression of a disease.

Protein Accumulation Diseases

As used herein "protein accumulation diseases" are diseases that are associated with protein accumulation and aggregation.

"Brain protein accumulation diseases" are associated with protein accumulation and aggregation in the brain. For example, Alzheimer's disease involves accumulation of the Aβ protein, Parkinson's disease involves accumulation of α-synuclein, Huntington's disease involves aggregation of mutated huntingtin proteins, and amyotrophic lateral sclerosis involves accumulation of mutated superoxide dismutase-1 proteins. Some chronic psychiatric disorders, such as schizophrenia, bipolar disorder, and recurrent major depression, have also been associated with protein aggregation. The reduction of protein accumulation events is important for slowing the progression of these diseases and disorders. Studies indicate that protein degradation processes that clear these aggregated proteins could provide treatment for some or all of these diseases and disorders.

As used herein, "Mild Cognitive Impairment" or "MCI" means an impairment in memory that is not severe enough to affect daily function and that is linked to a condition other than AD, other than Parkinson's disease, and other than Huntington's disease. MCI may comprise deficits in cognitive functions in addition to impaired memory. Subjects with MCI have actual memory loss, rather than the sometimes slow memory retrieval from relatively preserved memory storage in age-matched controls. MCI tends to first affect short-term (also called episodic) memory first. Subjects have trouble remembering recent conversations, the location of commonly used items, and appointments. However, memory for remote events is typically intact, as is attention (also called working memory—subjects can repeat lists of items and do simple calculations). MCI often progresses to dementia.

MCI is an aspect of cognitive aging that is also considered to be a transitional state between normal aging and the dementia into which it may convert. MCI has received increasing acceptance as a distinct stage between normal cognitive aging and dementia (See, e.g., Mariani et al., 2007; Petersen et al., 2009, the entire contents of each of which are hereby incorporated herein by reference). Regarding aspects of MCI, the reductions in the brain's use of glucose (i.e. glucose metabolism linked to neuronal activity) and hippocampal volume are often detected 10-15 years before the first sign of cognitive decline or memory loss (Bateman et al., 2012). The causes of MCI are not yet completely understood. Experts believe that many cases—but not all—result from brain changes occurring in the very early stages of Alzheimer's disease or other dementias, thus MCI-related brain changes are not restricted to being linked to Alzheimer's disease (AD) (see Fjell et al., 2013). The reduced brain function of MCI is a nuisance, and it can lead to significant impairment of a person's ability to learn new information, solve problems, or carry out everyday activities. In some embodiments of the invention, the progression of one or more, or all of the symptoms of MCI discussed above is slowed or reversed.

MCI causes greater memory loss than age-associated memory impairment; memory and sometimes other cognitive functions are worse in subjects with this disorder than in age-matched controls, but daily functioning is not affected. In contrast, dementia impairs daily functioning. Up to 50% of subjects with mild cognitive impairment develop dementia within 3 years. See, e.g., The Merck Manual, "Dementia" full review/revision April 2013 by Juebin Huang, MD, PhD, available from www.merckmanuals.com/professional/neurologic_disorders/delirium_and_dementia/dementia.html, the entire contents of which are hereby incorporated herein by reference.

As used herein, "dementia" means memory loss plus evidence of cognitive and behavioral dysfunction. A subject with dementia may have difficulty with finding words and/or naming objects (aphasia), doing previously learned motor activities (apraxia), or planning and organizing everyday tasks, such as meals, shopping, and bill paying (impaired executive function). A subject's personality may change; for example, the subject may become uncharacteristically irritable, anxious, agitated, and/or inflexible.

Clinical criteria for dementia include cognitive or behavioral (neuropsychiatric) symptoms that interfere with the ability to function at work or do usual daily activities. These symptoms represent a decline from previous levels of functioning. These symptoms are not explained by delirium or a major psychiatric disorder. In some embodiments, the cognitive or behavioral impairment involves ≥2 of the following domains: i) Impaired ability to acquire and remember new information (amnesia), ii) Language dysfunction (aphasia), iii) Visuospatial dysfunction (agnosia; eg, inability to recognize faces or common objects), iv) Impaired executive function, including reasoning, handling of complex tasks, and/or judgment (apraxia); v) Changes in personality, behavior, or comportment.

Dementia impairs cognition globally. Onset is gradual, although family members may suddenly notice deficits (e.g., when function becomes impaired). Often, loss of short-term memory is the first sign. Although symptoms of dementia exist in a continuum, they can be divided into early, intermediate, and late. Personality changes and behavioral disturbances may develop early or late. Motor and other focal neurologic deficits occur at different stages, depending on the type of dementia. Incidence of seizures is somewhat increased during all stages. Psychosis—hallucinations, delusions, or paranoia—occurs in about 10% of subjects with dementia, although a higher percentage may experience these symptoms temporarily.

During "early dementia" Recent memory is impaired; learning and retaining new information become difficult. Language problems (especially with word finding), mood swings, and personality changes develop. Subjects may have progressive difficulty with independent activities of daily living (e.g., balancing their checkbook, finding their way around, remembering where they put things). Abstract thinking, insight, or judgment may be impaired. Subjects may respond to loss of independence and memory with irritability, hostility, and agitation. Functional ability may be further limited by the following:

Agnosia: Impaired ability to identify objects despite intact sensory function.

Apraxia: Impaired ability to do previously learned motor activities despite intact motor function. Aphasia: Impaired ability to comprehend or use language.

Although early dementia may not compromise sociability, family members may report strange behavior accompanied by emotional lability. In embodiments of the invention, one, two, three, four, five, or more, or all of the symptoms of early dementia discussed above are reduced, reversed, or prevented. In some embodiments of the invention, the progression of one, two, three, four, five, or more, or all of the symptoms of early dementia discussed above is slowed or reversed.

In some embodiments, early dementia is linked to a condition other than AD, other than Parkinson's disease and other than Huntington's disease.

During "intermediate dementia" subjects become unable to learn and recall new information. Memory of remote events is reduced but not totally lost. Subjects may require help with basic activities of daily living (e.g., bathing, eating, dressing, toileting). Personality changes may progress. Subjects may become irritable, anxious, self-centered, inflexible, or angry more easily, or they may become more passive, with a flat affect, depression, indecisiveness, lack of spontaneity, or general withdrawal from social situations. Behavior disorders may develop: subjects may wander or become suddenly and inappropriately agitated, hostile, uncooperative, or physically aggressive.

By this stage, subjects have lost all sense of time and place because they cannot effectively use normal environmental and social cues. Subjects often get lost; they may be unable to find their own bedroom or bathroom. They often remain ambulatory but are at risk of falls or accidents secondary to confusion. Altered sensation or perception may culminate in psychosis with hallucinations and paranoid and persecutory delusions. Sleep patterns are often disorganized. In embodiments of the invention, one, two, three, four, five, or more, or all of the symptoms of intermediate dementia discussed above are reduced, reversed, or prevented. In some embodiments of the invention, the progression of one, two, three, four, five, or more, or all of the symptoms of intermediate dementia discussed above is slowed or reversed.

During "late dementia" subjects cannot walk, feed themselves, or do any other activities of daily living; they may become incontinent. Recent and remote memory is completely lost. Subjects may be unable to swallow. They are at risk of undernutrition, pneumonia (especially due to aspiration), and pressure ulcers. Because they depend completely on others for care, placement in a long-term care facility often becomes necessary. Eventually, subjects become mute. In embodiments of the invention, one, two, three, four, five, or more, or all of the symptoms of late dementia discussed above are reduced, reversed, or prevented. In some embodiments of the invention, the progression of one, two, three, four, five, or more, or all of the symptoms of late dementia discussed above is slowed or reversed.

End-stage dementia results in coma and death, usually due to infection.

Cytoplasmic deposition of α-synuclein is a common pathological feature of many neurodegenerative diseases collectively called α-synucleinopathies, including familial Parkinson's disease.

Parkinson's disease (Parkinson's) is a motor system disorder which is associated with the loss of dopamine-producing brain cells. Dopamine is necessary for coordinated muscle function and movement. Dopamine is normally produced by certain nerve cells (neurons) in the substantia nigra region of the brain; however, Parkinson's subjects experience a loss of these neurons which leads to impaired movement. This loss of neurons is associated with the accumulation of α-synuclein, a protein that is mutated and/or misfolded in Parkinson's and other diseases. The α-synuclein forms aggregates that accumulate in Lewy bodies, and which are seen in the brains of subjects who have died from Parkinson's.

The age-related neurodegenerative disorder Alzheimer's disease (AD) involves the accumulation of oligomeric species, protein aggregation, and altered brain function. One of the major hallmarks of AD is the plaque deposits consisting primarily of amyloid fibrils formed by the amyloid beta peptide Aβ1-42 as well as the buildup of soluble oligomers of this peptide. Mutations associated with familial AD, including mutations in the amyloid precursor protein (APP), strongly implicate Aβ1-42 as a causative factor since the mutations increase the relative amount of this Aβ peptide. Increased Aβ is one of the earliest events in AD, and, besides extracellular accumulation, Aβ oligomerization also occurs intraneuronally. Aβ oligomers disrupt synaptic plasticity, impair synaptic responses and memory, and cause cytotoxicity, as well as produce synaptic deterioration. Aβ oligomers, especially trimers and multiples of trimeric species, are particularly stable.

There are no current treatments to reduce the abnormal protein accumulation events in AD. Only two classes of drugs are approved for treating AD, acetyl-cholinesterase inhibitors and N-methyl-D-aspartic acid (NMDA) receptor antagonists. Both types of drugs only affect the symptoms of AD. Acetyl-cholinesterase inhibitors are for mild to moderate AD and have modest effects in a small percentage of subjects who take the drug, and are typically ineffective after 6-12 months of use. The NMDA receptor antagonist that is available treats the secondary pathology but not the protein accumulation in mild to severe AD.

The neurodegenerative disorder Huntington's disease (Huntington's) is caused by a trinucleotide repeat expansion in the huntingtin gene which codes for huntingtin protein, "Htt." People who have Huntington's disease have more C-A-G codons on their huntingtin gene which results in Htts that are "altered" or abnormal in that they have an excess number of glutamines. As a result of the excess glutamines, these altered Htts form protein aggregates which can interfere with nerve cell function.

Amyotrophic lateral sclerosis (ALS) is a progressive neurodegenerative disease that attacks nerve cells in the brain and the spinal cord. Neuronal cell death has been linked to the presence of aggregates of mutant superoxide dismutase-1 (SOD1) protein. Mutant SOD1 accumulates to form high molecular weight amorphous aggregates which can interact with other proteins. When these mutant SOD1 proteins accumulate and form aggregates in a neuronal cell, the cell almost always dies.

Aspects of the present invention relate to the discovery that PADK and other compounds of the invention increase cathepsin B in eye tissue. Some embodiments of the invention are useful for treating retinal or optic nerve disease or damage in subjects.

Age-related macular degeneration (AMD) is the most common cause of irreversible vision loss in the elderly. Age-related macular degeneration (AMD) is characterized by the presence of drusen, which are extracellular deposits that accumulate beneath the retinal pigmented epithelium. Many protein and lipid constituents of drusen are similar to those found in deposits characteristic of other age-related degenerative disorders such as Alzheimer's disease (AD) and other amyloid diseases. These include amyloid β (Aβ), vitronectin, amyloid P, apolipoprotein E, and inflammatory mediators such as acute phase reactants and complement components (Isas et al 2010). AMD may be dry or wet AMD.

Dry AMD causes the tissues of the macula to thin as cells disappear. Accumulated waste products from the rods and cones may produce deposits in the retina (the transparent, light-sensitive structure at the back of the eye) called drusen (yellow spots). Both eyes may be affected simultaneously in the dry form. There is no evidence of scarring or of bleeding or other fluid leakage in the macula. In dry AMD, the loss of central vision occurs slowly and painlessly over years. Subjects may have few or no symptoms but, when they do have symptoms, they often occur in both eyes. Objects may appear washed out, fine detail may be lost, and reading may become more difficult. As the disease progresses, central blind spots (scotomas) usually occur and can sometimes severely impair vision. Most subjects retain enough vision to read and drive. In some embodiments of the invention, the progression of one, two, three, four, five, or more, or all of the symptoms of dry AMD discussed above is slowed or reversed.

Wet AMD can result from dry AMD. AMD always begins as dry AMD. Some subjects develop wet AMD as well when abnormal blood vessels grow in from the choroid (the layer of blood vessels that lies between the retina and the outer white layer of the eye called the sclera) under the macula and leak blood and fluid (hence the description as "wet"). Eventually, a mound of scar tissue develops under the macula. The wet form develops in one eye first but eventually may affect both eyes. In wet AMD, loss of vision tends to progress quickly, usually over days or weeks, and may be even more sudden if one of the abnormal blood vessels bleeds. The first symptom may be an area of blurry, wavy, or distorted central vision. Vision at the outer edges of the visual field (peripheral vision) is typically not affected. Wet AMD usually affects one eye at a time. Often, difficulty with reading or watching television results. In some embodiments of the invention, the progression of one, two, three, four, five, or more, or all of the symptoms of wet AMD discussed above is slowed or reversed. See, e.g., The Merck Manual, "Age-Related Macular Degeneration" full review/revision April 2013 by Juebin Huang, MD, PhD, available from www.merckmanuals.com.

As used herein, "an amount that is effective to treat the subject" or "therapeutically effective amount" when referring to an amount of a compound refers to the quantity of the compound that is sufficient to yield a desired therapeutic response without undue adverse side effects (such as toxicity, irritation, or allergic response) commensurate with a reasonable benefit/risk ratio when used in the manner of this invention. It will be understood that the specific effective amount will vary with such factors as the particular condition being treated, the physical condition of the subject, the type of subject being treated, the duration of the treatment, the nature of concurrent therapy (if any), and the specific formulations employed and the structure of the compound or its derivatives.

Non-limiting examples of diagnostic tests that are useful in embodiments of the invention are a cognitive test, a family history assessment, a blood test, a cerebrospinal fluid test (CSF), a neuronal connectivity scan, white matter integrity analysis, an magnetic resonance imaging (MRI) test of gray matter, an assessment of the microstructural integrity of axons and their surrounding myelin, a glucose metabolism assessment, a cortical thickness analysis, a multimodality biomarker assessment, genomic analysis, a sarcasm detection assessment, or any combination thereof. In some embodiments, the subject has an indication that warrants prophylactic treatment. In some embodiments relating to MCI, the indication is a reduction in glucose use in the brain of the subject, is a reduction in hippocampal volume in the brain of the subject, or decreased expression of synaptophysin, AMPA-type glutamate receptor subunit GluR1, or an acetylcholinesterase (AChE) enzyme isoform, relative to i) a previous level of expression of synaptophysin, AMPA-type glutamate receptor subunit GluR1, or the AChE enzyme isoform in the subject, or ii) the level of expression of synaptophysin, AMPA-type glutamate receptor subunit GluR1, or the AChE enzyme isoform in subjects not afflicted with MCI.

The compounds used in the methods and compositions of the present invention may be in a salt form. As used herein, a "salt" is a salt of the instant compounds which has been modified by making acid or base salts of the compounds. In the case of compounds used to treat cancer, the salt is pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1-19).

Administration

"Administering" one or more compounds used in methods of the subject invention can be effected or performed using any of the various methods and delivery systems known to those skilled in the art. The administering can be, for example, intravenous, oral, intramuscular, intravascular, intra-arterial, intracoronary, intramyocardial, intraperitoneal, and subcutaneous. Other non-limiting examples include topical administration, or coating of a device to be placed within the subject. In embodiments, administration is effected by injection or via a catheter.

The compounds used in the methods of the present invention may be administered in various forms, including those detailed herein.

The present invention provides methods of treating a disease in which a compound is administered as a monotherapy. The present invention also provides methods in which administration with a compound is supplemented with another, adjunct therapy in a subject afflicted with a disease. In some embodiments, the treatment with the compound may be administered with an adjunct therapy, i.e. the subject or subject in need of the compound is treated with or given another drug for the disease together with the compound. Treatment with the compound and the adjunct therapy can be sequential where the subject is treated first with one drug and then the other or the two drugs are given simultaneously. These can be administered independently by the same route or by two or more different routes of administration depending on the dosage forms employed.

Injectable drug delivery systems may be employed in the methods described herein include solutions, suspensions, gels. Oral delivery systems include tablets and capsules. These can contain excipients such as binders (e.g., hydroxypropylmethylcellulose, polyvinyl pyrilodone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc). Solutions, suspensions and powders for reconstitutable delivery systems include vehicles such as suspending agents (e.g., gums, zanthans, cellulosics and sugars), humectants (e.g., sorbitol), solubilizers (e.g., ethanol, water, PEG and propylene glycol), surfactants (e.g., sodium lauryl sulfate, Spans, Tweens, and cetyl pyridine), preservatives and anti-oxidants (e.g., parabens, vitamins E and C, and ascorbic acid), anti-caking agents, coating agents, and chelating agents (e.g., EDTA).

The dosage of the compounds administered in treatment will vary depending upon factors such as the pharmacodynamic characteristics of a specific agent and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect.

A dosage unit of the compounds used in the methods of the present invention may comprise a single compound or mixtures thereof with additional agents. The compounds can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by injection, topical application, or other methods, into or onto a site of administration, all using dosage forms well known to those of ordinary skill in the pharmaceutical arts.

The compounds used in the methods of the present invention can be administered in a pharmaceutically acceptable carrier. As used herein, a "pharmaceutically acceptable carrier" is a pharmaceutically acceptable solvent, suspending agent or vehicle, for delivering the compounds to the subject, such as to an animal or human subject. The carrier may be liquid or solid and is selected with the planned manner of administration in mind. Liposomes are also a pharmaceutically acceptable carrier. The compounds used in the methods of the present invention can be administered in admixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. The unit will be in a form suitable for oral, rectal, topical, intravenous or direct injection or parenteral administration. The compounds can be administered alone or mixed with a pharmaceutically acceptable carrier. This carrier can be a solid or liquid, and the type of carrier is generally chosen based on the type of administration being used. The active agent can be co-administered in the form of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

Techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol. 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol 40 (Gilbert S. Banker, Christopher T. Rhodes, Eds.). All of the aforementioned publications are incorporated by reference herein.

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds used in the method of the present invention may also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines. The compounds may be administered as components of tissue-targeted emulsions.

The compounds used in the methods of the present invention may also be coupled to soluble polymers as targetable drug carriers or as a prodrug. Such polymers include polyvinylpyrrolidone, pyran copolymer, polyhydroxylpropylmethacrylamide-phenol, polyhydroxyethylaspartamidephenol, or polyethyleneoxide-polylysine substituted with palmitoyl residues. Furthermore, the compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient compounds and powdered carriers, such as lactose, starch, cellulose derivatives, magnesium stearate, stearic acid, and the like. Similar diluents can be used to make compressed tablets. Both tablets and capsules can be manufactured as immediate release products or as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

For oral administration in liquid dosage form, the oral drug components are combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents.

Liquid dosage forms for oral administration can contain coloring and flavoring to increase subject acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in this field.

The compounds used in the methods of the present invention may also be administered in intranasal form via use of suitable intranasal vehicles, or via transdermal routes, using those forms of transdermal skin patches well known to those of ordinary skill in that art. To be administered in the form of a transdermal delivery system, the dosage administration will generally be continuous rather than intermittent throughout the dosage regimen.

Parenteral and intravenous forms may also include minerals and other materials to make them compatible with the type of injection or delivery system chosen.

All publications and other references mentioned herein are incorporated by reference in their entirety, as if each individual publication or reference, were specifically and individually indicated to be incorporated by reference. Publications and references cited herein are not admitted to be prior art.

This invention will be better understood by reference to the Experimental Details which follow, but those skilled in the art will readily appreciate that the specific experiments detailed are only illustrative of the invention as defined in the claims which follow thereafter.

EXPERIMENTAL DETAILS

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only.

Example 1. Cathepsin B Positive Modulation by Flavonols—Members of the Flavonoid Class of Polyphenolic Compounds As described in FIG. 1, flavonols such as quercetin (Q), fisetin (F), and myricetin (M) were applied daily to rodent hippocampal slice cultures. After two (2) days, non-treated (NT) and treated slices were harvested, homogenates were prepared, and equal protein aliquots were assessed by immunoblot to label the 30-kDa active form of cathepsin B (CatB-30).

Statistically significant increases in cathepsin B were produced by 5-20 µM quercetin (1.96-fold) and by 5-30 µM fisetin (1.65-fold).

Example 2. Cathepsin B Positive Modulation by Z-Phe-Pro-OH

Figure 2:
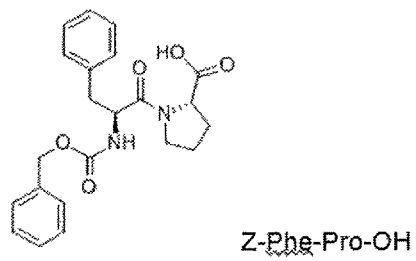
FIG. 2. Cathepsin B positive modulation by Z-Phe-Pro-OH. The compound Z-Phe-Pro-OH was applied to rodent hippocampal slice cultures for two (2) days. Compared to non-treated (NT) slices using immunoblotting, the 30-kDa active form of cathepsin B (CatB-30) was increased 1.55 to 3.66 fold.

As described in FIG. 2, the compound of Z-Phe-Pro-OH was applied to rodent hippocampal slice cultures for two (2) days.

Compared to non-treated (NT) slices using immunoblotting, the 30-kDa active form of cathepsin B (CatB-30) was increased 1.55 to 3.66 fold.

Example 3. Quercetin Enhances the Effect of the Cathepsin B Positive Modulator Z-Phe-Ala-diazomethylketone (PADK)

Figure 3:
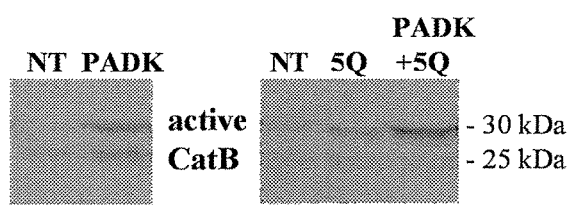
FIG. 3. Quercetin enhances the effect of the cathepsin B positive modulator Z-Phe-Ala-diazomethylketone (PADK). Quercetin (Q) at 5 µM was added to the daily PADK treatments of rodent hippocampal slice cultures. After two (2) days, non-treated (NT) and treated slices were harvested, homogenates were prepared, and equal protein aliquots were assessed by immunoblot to label the active form of cathepsin B (CatB-30). Paired, two-tailed t-test among distinct immunoblots found a statistically significant enhancement of the PADK effect by quercetin (p=0.0167; pairing was effective: p=0.0014). An enhancement of 60-70% occurred, whereas 5 µM quercetin alone for 2 days caused only a 21% increase in CatB-30.
Figure 3:
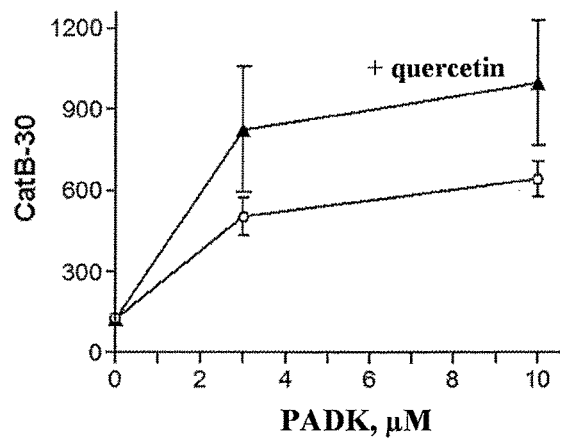

As described in FIG. 3, the flavonol of quercetin (Q) was added at 5 µM to the daily PADK treatments of rodent hippocampal slice cultures. After two (2) days, non-treated (NT) and treated slices were harvested, homogenates were prepared, and equal protein aliquots were assessed by immunoblot to label the active form of cathepsin B (CatB-30).

Paired, two-tailed t-test among distinct immunoblots found a statistically significant enhancement of the PADK effect by quercetin ($p=0.0167$; pairing was effective:

p=0.0014). An enhancement of 60-70% occurred, whereas 5 μM quercetin alone for 2 days caused only a 21% increase in CatB-30.

Example 4. Fisetin and Myricetin Enhance the Cathepsin B Positive Modulation Produced by 104M Z-Phe-Ala-diazomethylketone (PADK)

Figure 4:
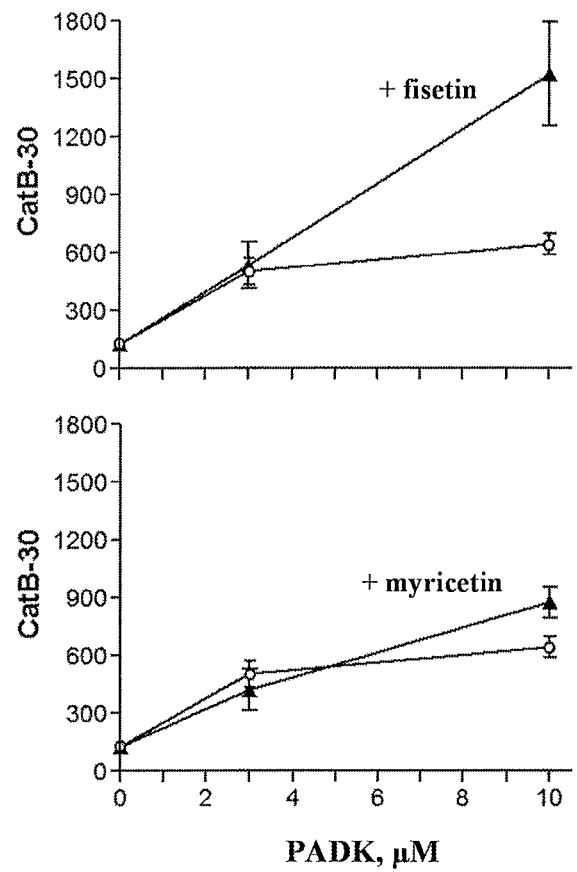
FIG. 4. Fisetin and myricetin enhance the cathepsin B positive modulation produced by 10 µM Z-Phe-Ala-diazomethylketone (PADK). Fisetin at 5 µM (top graph) or myricetin at 5 µM (bottom graph) were added to the two daily PADK treatments of rodent hippocampal slice cultures. The non-treated (NT) and treated slices were harvested, homogenates were prepared, and equal protein aliquots were assessed by immunoblot to label the active form of cathepsin B (CatB-30). At the 10 µM PADK concentration, analyses found a statistically significant enhancement of the PADK effect by fisetin (two-tailed p=0.0014) and a smaller enhancement by myricetin (one-tailed p=0.033). An enhancement of 95-140% was produced by fisetin, whereas 5 µM fisetin alone for two (2) days caused only a 40% increase in CatB-30.

As described in FIG. 4, the flavonols of fisetin at 5 μM (top graph of FIG. 4) or myricetin at 5 μM (bottom graph of FIG. 4) were added to the two daily PADK treatments of rodent hippocampal slice cultures. The non-treated (NT) and treated slices were harvested, homogenates were prepared, and equal protein aliquots were assessed by immunoblot to label the active form of cathepsin B (CatB-30).

At the 10 μM PADK concentration, analyses found a statistically significant enhancement of the PADK effect by fisetin (two-tailed p=0.0014) and a smaller enhancement by myricetin (one-tailed p=0.033). An enhancement of 95-140% was produced by fisetin, whereas 5 μM fisetin alone for two (2) days caused only a 40% increase in CatB-30.

Example 5. Dose-Dependent Enhancement of the PADK Effect on CatB by Flavonols

Figure 5:
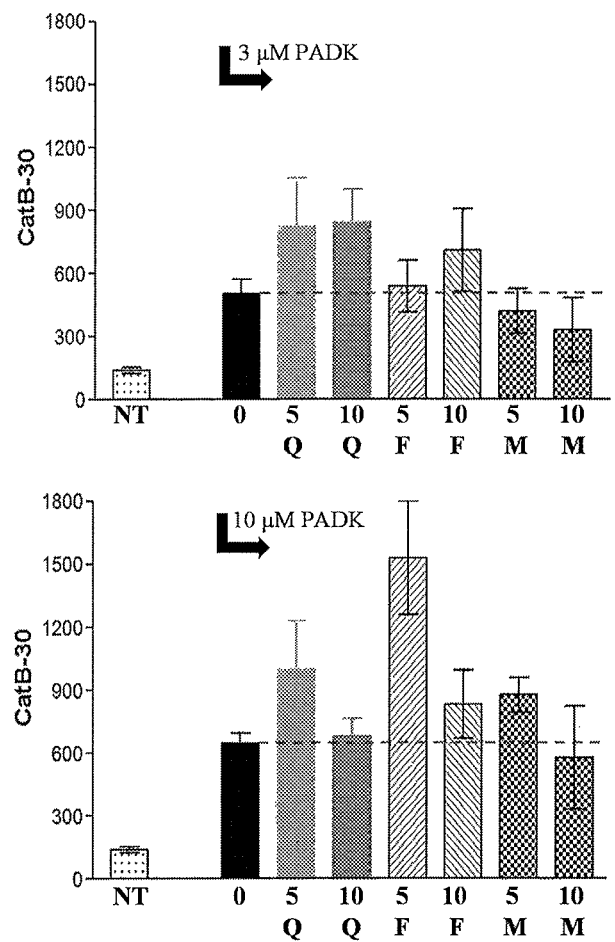
FIG. 5. Dose-dependent enhancement of the PADK effect on CatB by flavonols. Quercetin (Q), fisetin (F), and myricetin (M) at 5-10 µM were applied daily to rodent hippocampal slice cultures that were also treated with 3 µM PADK (top graph) or 10 µM PADK (bottom graph). After two (2) days, non-treated (NT) and treated slices were harvested, homogenates were prepared, and equal protein aliquots were assessed by immunoblot to label the 30-kDa active form of cathepsin B (CatB-30). Note at 3 µM PADK, i) both 5 and 10 µM quercetin enhanced the PADK effect, ii) only the higher 10 µM concentration of fisetin enhanced the effect, and iii) myricetin had no enhancing effect at either concentration. The 10 µM PADK slices indicate that each flavonol at the lower concentration has an enhancing effect, but the effect is eliminated or reduced when the flavonol concentration is doubled.

As described in FIG. 5, the flavonols of quercetin (Q), fisetin (F), and myricetin (M) at 5-10 μM were applied daily to rodent hippocampal slice cultures that were also treated with 3 μM PADK (top graph) or 10 μM PADK (bottom graph). After two (2) days, non-treated (NT) and treated slices were harvested, homogenates were prepared, and equal protein aliquots were assessed by immunoblot to label the 30-kDa active form of cathepsin B (CatB-30).

Note at 3 μM PADK, i) both 5 and 10 μM quercetin enhanced the PADK effect, ii) only the higher 10 μM concentration of fisetin enhanced the effect, and iii) myricetin had no enhancing effect at either concentration. The 10 μM PADK slices indicate that each flavonol at the lower concentration has an enhancing effect, but the effect is eliminated or reduced when the flavonol concentration is doubled.

Note that the aforementioned micromolar (μM) amounts applied to rodent hippocampal slice cultures generally correspond to a range of 3-20 mg/kg for PADK and 10-30 mg/kg for flavonols of quercetin, fisetin, and myricetin in terms of human dosing amounts.

Example 6: In Vivo Similarities Between PADK and Quercetin Effects in the Brain

Compounds in peanut butter pellets were administered to middle-aged mice orally twice daily for 11 days, then dissected hippocampi were compared to control mice that received the same oral dosing with control compound. The results are summarized in Table 1 below.

TABLE 1

In vivo similarities between PADK
and quercetin effects in the brain

| PADK effect | Quercetin effect |
|---|---|
| increased CatB-30 in male mice | increased CatB-30 in male mice |
| increased CatB-30 in female mice | increased CatB-30 in female mice |

TABLE 1-continued

In vivo similarities between PADK
and quercetin effects in the brain

| PADK effect | Quercetin effect |
|---|---|
| enhanced synaptic marker GluR1 | enhanced synaptic marker GluR1 |
| levels of actin were unchanged | levels of actin were unchanged |

DISCUSSION

The present application details several significant findings.

Firstly, flavonols including quercetin, fisetin, and myricetin were shown to increase levels of cathepsin B.

Secondly, the compound of Z-Phe-Pro-OH was shown to increase levels of cathepsin B.

Thirdly, flavonols including quercetin, fisetin, and myricetin were shown to enhance the effect of the cathepsin B positive modulator Z-Phe-Ala-diazomethylketone (PADK). In other words, the present application details a surprising finding that the compound of PADK has an enhanced effect on cathepsin B when utilized in combination with flavonols, particularly those referenced above. Moreover, the compound of PADK is as effective at a lower dosage when utilized in this combination as compared to a higher dosage of PADK alone.

What is claimed is:

1. A method for treating a subject afflicted with Alzheimer's disease, Parkinson's disease, Huntington's disease, amyotrophic lateral sclerosis, Mild Cognitive Impairment (MCI), or traumatic brain injury (TBI), the method comprising administering to the subject a phenylalanyl proline compound having the structure:

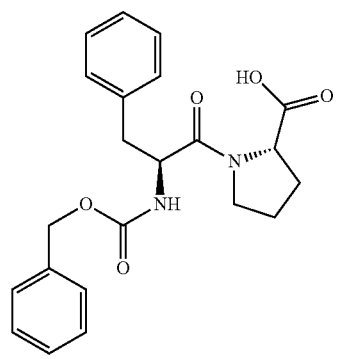 [SMILES: O=C(N[C@@H](Cc1ccccc1)C(=O)N1CCC[C@H]1C(=O)O)OCc1ccccc1]

or an analogue thereof, or a pharmaceutically acceptable salt or ester thereof;
and
further comprising administering to the subject one, two, three, or more of:
 i) N-carbobenzoxy-phenylalanyl-alanyl-diazomethylketone (PADK) or a PADK analogue, or a pharmaceutically acceptable salt or ester thereof;
 ii) N-carbobenzoxy-phenylalanyl-phenylalanyl-diazomethylketone (PPDK) or a pharmaceutically acceptable salt or ester thereof;

iii) a PADK analogue having the structure:

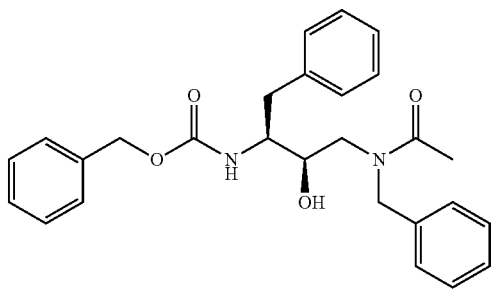 [SMILES: CC(=O)N(Cc1ccccc1)C[C@@H](O)[C@H](Cc1ccccc1)NC(=O)OCc1ccccc1]

or a pharmaceutically acceptable salt or ester thereof;
iv) a PADK analogue having the structure:

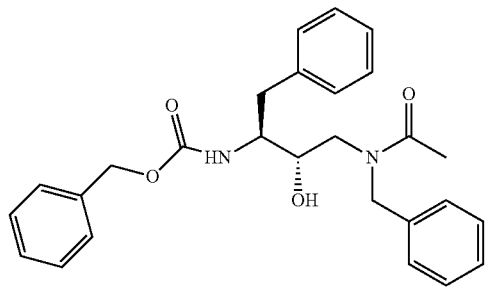 [SMILES: CC(=O)N(Cc1ccccc1)C[C@H](O)[C@H](Cc1ccccc1)NC(=O)OCc1ccccc1]

or a pharmaceutically acceptable salt or ester thereof;
v) a PADK analogue having the structure:

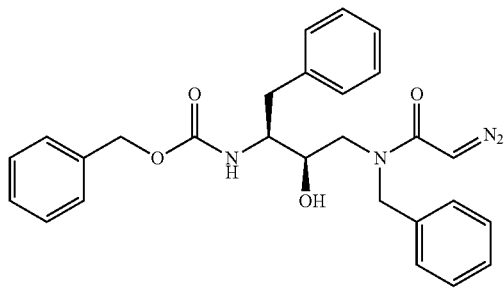

or a pharmaceutically acceptable salt or ester thereof; or
vi) a flavonoid,
each in an amount that when administered together is effective to treat the subject.

2. The method of claim 1, wherein the subject is afflicted with Alzheimer's disease, Huntington's disease, Parkinson's disease, or amyotrophic lateral sclerosis.

3. The method of claim 1, wherein the subject is afflicted with TBI.

4. The method of claim 1, wherein the phenylalanyl proline compound is administered to the subject parenterally, by inhalation, intranasally, topically, subcutaneously, intramuscularly, rectally or by intrapulmonary injection.

5. The method of claim 4, wherein the phenylalanyl proline compound is orally administered to the subject.

6. The method of claim 1, wherein the phenylalanyl proline compound is administered to the subject in a pharmaceutically acceptable carrier.

7. The method of claim 1, wherein the flavonoid is:
a) quercetin or a quercetin analogue,
b) fisetin or a fisetin analogue, or
c) myricetin or a myricetin analogue.

8. A method for treating a subject afflicted with Alzheimer's disease, Parkinson's disease, Huntington's disease, amyotrophic lateral sclerosis, Mild Cognitive Impairment (MCI), or traumatic brain injury (TBI), the method comprising administering to the subject an amount of a first compound and an amount of a second compound, wherein the first compound is N-benzyloxy-phenylalanyl-alanyl-diazomethylketone (PADK) or a PADK analogue, or a pharmaceutically acceptable salt or ester thereof, and wherein the second compound is a phenylalanyl proline compound having the structure:

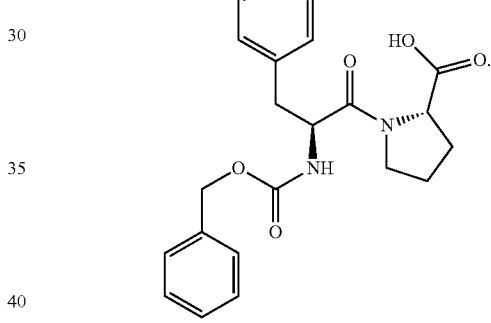

or an analogue thereof, or a pharmaceutically acceptable salt or ester thereof.

9. The method of claim 8, further comprising administering to the subject a flavonoid.

10. The method of claim 8, wherein the subject is afflicted with Alzheimer's disease, Huntington's disease, Parkinson's disease, or amyotrophic lateral sclerosis.

11. The method of claim 8, wherein the subject is afflicted with TBI.

12. The method of claim 9, wherein the flavonoid is:
a) quercetin or a quercetin analogue,
b) fisetin or a fisetin analogue, or
c) myricetin or a myricetin analogue.

* * * * *